(12) United States Patent
Zheng et al.

(10) Patent No.: US 10,669,370 B2
(45) Date of Patent: Jun. 2, 2020

(54) BENZYLATED MANNICH BASE CURING AGENTS, COMPOSITIONS, AND METHODS

(71) Applicant: Evonik Operations GmbH, Essen (DE)

(72) Inventors: Shiying Zheng, Center Valley, PA (US); Gamini Ananda Vedage, Bethlehem, PA (US); Marcelo Rufo, Sao Paulo (BR); Daniel Iliev Totev, De Meern (NL); Michael Cook, De Meern (NL)

(73) Assignee: Evonik Operations GmbH, Essen (DE)

( * ) Notice: Subject to any disclaimer, the term of this patent is extended or adjusted under 35 U.S.C. 154(b) by 29 days.

(21) Appl. No.: 15/439,293

(22) Filed: Feb. 22, 2017

(65) Prior Publication Data

US 2017/0240691 A1    Aug. 24, 2017

Related U.S. Application Data

(60) Provisional application No. 62/298,019, filed on Feb. 22, 2016.

(51) Int. Cl.
| | |
|---|---|
| *C08G 59/50* | (2006.01) |
| *C07C 211/01* | (2006.01) |
| *C07C 209/68* | (2006.01) |
| *C08G 59/62* | (2006.01) |
| *C08G 73/02* | (2006.01) |
| *C09D 163/00* | (2006.01) |

(52) U.S. Cl.
CPC ........ *C08G 59/5033* (2013.01); *C07C 209/68* (2013.01); *C07C 211/01* (2013.01); *C08G 59/502* (2013.01); *C08G 59/623* (2013.01); *C08G 73/0206* (2013.01); *C09D 163/00* (2013.01)

(58) Field of Classification Search
CPC ..................................................... C08G 59/40
See application file for complete search history.

(56) References Cited

U.S. PATENT DOCUMENTS

| | | | |
|---|---|---|---|
| 4,269,742 A | 5/1981 | Goeke et al. | |
| 5,280,091 A | 1/1994 | Dubowik et al. | |
| 6,465,601 B1 * | 10/2002 | Wiesendanger ... | C08G 18/1816 525/453 |
| 8,143,331 B2 | 3/2012 | Raymond et al. | |
| 8,147,964 B2 | 4/2012 | Vedage et al. | |
| 8,168,296 B2 * | 5/2012 | Vedage .............. | C08G 18/3256 428/413 |
| 8,735,512 B2 | 5/2014 | Walker et al. | |

FOREIGN PATENT DOCUMENTS

| | | |
|---|---|---|
| EP | 2151461 A2 | 2/2010 |
| EP | 2546230 A1 | 1/2013 |
| WO | 2016023839 A1 | 2/2016 |

OTHER PUBLICATIONS

PCT International Search Report dated May 23, 2017 corresponding to PCT International Application No. PCT/US2017/018853 filed Feb. 22, 2017 (5 pages).

* cited by examiner

*Primary Examiner* — Kuo Liang Peng
(74) *Attorney, Agent, or Firm* — Andrew H. Chung; Linda S. Li; Jason S. Ngui

(57) ABSTRACT

Compositions and curing agents comprising a benzylated Mannich base composition. The benzylated Mannich base composition includes a reaction product of (a) a substituted phenolic compound having at least one substituent of formula (I):

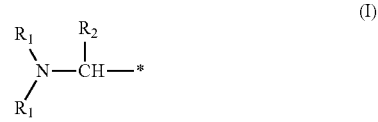

wherein $R_1$ is each independently a linear or branched alkyl group having 1 to 4 carbon atoms, and $R_2$ is hydrogen, methyl, ethyl or phenyl, with (b) a benzylated polyalkylene polyamine (II):

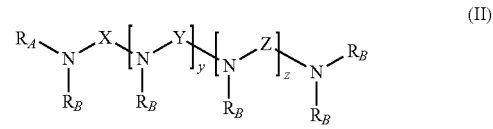

wherein $R_A$ is substituted or unsubstituted benzyl; $R_B$ is each independently $R_A$, or a hydrogen atom, or a group selected from $C_1$-$C_{16}$ linear, cyclic, and branched alkyl, alkenyl, and alkaryl groups; X, Y, and Z are independently selected from $C_2$-$C_{10}$ alkylene, and cycloalkylene groups; y is an integer from 0 to 7, and z is an integer from 0 to 4; and, optionally, (c) a multifunctional amine. Amine-epoxy compositions and articles produced from these compositions are also disclosed.

19 Claims, No Drawings

BENZYLATED MANNICH BASE CURING AGENTS, COMPOSITIONS, AND METHODS

CROSS-REFERENCE TO RELATED APPLICATIONS

This application claims the benefit of Provisional U.S. Patent Application Ser. No. 62/298,019, filed on Feb. 22, 2016, the disclosure of which is incorporated herein by reference in its entirety.

BACKGROUND OF THE INVENTION

The present invention provides benzylated amine Mannich base compositions, epoxy curing agents and amine-epoxy compositions derived from such compounds, and articles produced from such compounds and/or compositions.

Epoxies are known for their excellent adhesion, chemical and heat resistance, good-to-excellent mechanical properties, and good electrical insulating properties. Cured epoxy resin systems have found extensive applications ranging from coatings, adhesives, and composites. Specific examples include epoxy composites using carbon fiber and fiberglass reinforcements, protective coatings for metal surfaces, and construction products for concrete, cementitious or ceramic substrates, often referred to as civil engineering applications, such as formulations for concrete flooring.

Cured epoxy resin systems consist of two components that chemically react with each other to form a cured epoxy, which is a hard, duroplastic material. The first component is an epoxy resin and the second component is a curing agent, often referred to as a hardener. Epoxy resins are substances or mixtures which contain epoxide groups. The curing agents include compounds which are reactive to the epoxide groups of the epoxy resins, such as amines, carboxylic acid, and mercaptans (H. Lee and K. Neville "Handbook of Epoxy Resins" McGraw Hill, New York, 1967, pages 5-1 to 5-24). The epoxy resins may be cross-linked or cured by curing agents. The curing process is the chemical reaction of the epoxide groups in the epoxy resins and the reactive groups in the curing agents. The curing converts the epoxy resins, which have a relatively low molecular weight, into relatively high molecular weight materials by chemical addition of the curing agents to the epoxy resins. Additionally, the curing agent may contribute to many of the properties of the cured epoxy.

With the constant need in the coatings industry to comply with stricter volatile organic content (VOC) regulations, many two component epoxy systems now require the use of low molecular weight epoxy resins which are liquids at room temperature and free from solvents. The use of these resins can lead to several application and performance problems, for example, in coating applications, amine-epoxy compositions based on liquid resins tend to cure much more slowly than a comparable solvent based solid epoxy resin formulation and this problem becomes more severe at lower cure temperatures. Shipyards, for example, often reside in locations with cold winters, and paint must be applied when temperatures are at or below 5° C. Certain amine-epoxy formulations cure very slowly at these temperatures, often requiring at least 24 hours cure before reaching a point where coated structures can be handled or recoated with a second or third coating. In addition, at these application temperatures, many epoxy coatings suffer from problems referred to in the industry as blush, carbamate and exudate during the curing process.

These problems, in part are due to the incompatibility of the amine curing agent and epoxy resin, which cause phase separation and result in amine migration to the coating surface. In primary amines, the migratory amine can react with carbon dioxide ($CO_2$) and moisture present in the air resulting in carbamation. Whether in the form of carbamation or the greasy surface layer, referred to as exudate, these surface defects detract from the appearance of the coating and can lead to intercoat adhesion failures if the initial coating is overcoated. These problems are generally worse for coatings applied and cured under conditions of extreme cold and high humidity, where the amine-epoxy compatibility within the coating matrix is reduced.

Even with good compatibility between amine and epoxy, many epoxy curing agents suffer from slow cure at low temperature and only incomplete cure takes place. Slow cure requires longer time for coating to set and dry which means longer time to return to service or for the subsequent layer to be coated.

There are numerous amine-based curing agents and amine-epoxy compositions that are employed in the amine-epoxy coating industry; including polyamides, amine adducts and Mannich bases (including phenalkamines), however, none of these known products completely addresses the needs or solves the problems noted above. U.S. Pat. No. 4,269,742 discloses the preparation and use of Mannich base compounds as epoxy hardener to produce tack-free films at low temperature. U.S. Pat. No. 6,465,601 discloses Mannich base compounds as accelerators for curable epoxy and polyurethane systems. U.S. Pat. No. 8,735,512 discloses the preparation and use of Mannich base compounds based on N,N'-dimethyl secondary diamine polymers.

A Mannich base is a reaction product of an aldehyde, a phenol compound, and an amine. While certain Mannich bases can be used in amine-epoxy formulations, they are also not without drawbacks. Mannich bases can provide the productivity benefits of faster cure, however, the nature of the amines employed in such compositions means certain Mannich bases still suffer from blush, carbamation and exudate formation. In addition, depending upon the synthesis route adopted, the resultant Mannich base compound may contain unacceptable amounts of residual phenol. Phenol is a toxic chemical and its presence at levels greater than 1% in a chemical mixture can require special handling and disposal procedures to protect workers and the environment.

It has now been found that the benzylated Mannich base compositions of the present invention described herein below are suitable for use as curing agents in curable epoxy systems to improve or overcome the incompatibility between amine and epoxy, and the slow amine epoxy reaction rate at low temperature. They are readily miscible with the epoxy resins and positively influence the properties of the cured systems. The benzylated Mannich base compositions, according to the present invention, may also have the advantage of comparatively low viscosity. The lower viscosity reduces the need to use organic compounds to adjust the viscosity, thus reduces the use of volatile organic compounds (VOC) to comply with governmental VOC regulations. In addition, the new benzylated Mannich base compositions are also free from residual phenol and thus provide added environmental and worker safety benefits.

The disclosure of the foregoing publications, including patents and patent applications, is hereby incorporated by reference.

BRIEF SUMMARY OF THE INVENTION

The present invention discloses benzylated Mannich base compositions, curing agent compositions and methods of making such compounds, and compositions. These curing-agent compositions may be used to cure, harden, and/or crosslink an epoxy resin. The present invention comprises benzylated Mannich base compositions having at least two nitrogen atoms, at least two active amine hydrogen atoms and at least one benzyl group per molecule.

One embodiment, according to the present disclosure, includes a benzylated Mannich base composition including at least one benzylated Mannich base compound having at least two nitrogen atoms, at least two active amine hydrogen atoms and at least one benzyl group per molecule comprise the reaction product of an amine-exchange reaction by reacting:

(a) a substituted phenolic compound (Mannich base) having at least one substituent of formula (I):

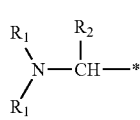

wherein $R_1$ is each independently a linear or branched alkyl group having 1 to 4 carbon atoms, and $R_2$ is hydrogen, methyl, ethyl or phenyl; with (b) a benzylated polyalkylene polyamine having at least two nitrogen atoms, at least two active amine hydrogen atoms and at least one benzyl group of formula (II):

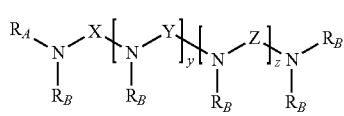

wherein $R_A$ is substituted or unsubstituted benzyl; $R_B$ is each independently $R_A$, or a hydrogen atom, or a group selected from $C_1$-$C_{16}$ linear, cyclic, and branched alkyl, alkenyl, and alkaryl groups; X, Y, and Z are independently selected from $C_2$-$C_{10}$ alkylene, and cycloalkylene groups; y is an integer from 0 to 7, and z is an integer from 0 to 4; and (c) optionally, a multifunctional amine having at least two nitrogen atoms, at least two active amine hydrogen atoms per molecule.

The present invention relates also to a process for the preparation of the benzylated Mannich base compositions by means of an amine exchange reaction by reacting:

(a) a substituted phenolic compound (known as Mannich base) having at least one substituent of formula (I); with (b) a benzylated polyalkylene polyamine having at least two nitrogen atoms, at least two active amine hydrogen atoms and at least one benzyl group of formula (II), and (c) optionally, a multifunctional amine having at least two nitrogen atoms, at least two active amine hydrogen atoms per molecule.

In a particular embodiment, the benzylated polyalkylene polyamine is benzylated polyethylene polyamine, benzylated polypropylene polyamine, benzylated polyethylene-polypropylene polyamine, and/or combinations thereof. Examples of benzylated polyethylene polyamine are benzylated ethylene diamine, benzylated diethylenetriamine, benzylated tetraethylenepentamine, and benzylated triethylenetetramine.

In other embodiments, the present invention includes curing agent compositions including benzylated Mannich base compounds having at least two nitrogen atoms, at least two active amine hydrogen atoms and at least one benzyl group per molecule, and the use of such curing agent compositions for curable epoxy.

In one aspect, embodiments of the present invention include a curing agent composition comprising the contact product of:

(a) the benzylated Mannich base composition having at least one benzylated Mannich base compound having at least two nitrogen atoms, at least two active amine hydrogen atoms, and at least one benzyl group per molecule, and (b) at least one multifunctional amine having two or more active amine hydrogens per molecule.

Generally, curing agent compositions of the present invention include an amine hydrogen equivalent weight (AHEW) based on 100% solids from about 30 to about 500.

Another aspect of the present invention includes amine-epoxy compositions and the cured products produced therefrom. For example, an amine-epoxy composition, in accordance with the present invention, includes the reaction product of:

(a) a curing agent composition comprising the benzylated Mannich base composition having at least one benzylated Mannich base compound having at least two nitrogen atoms, at least two active amine hydrogen atoms, and at least one benzyl group per molecule; and (b) an epoxy composition comprising at least one multifunctional epoxy resin.

Yet another aspect of the present invention includes amine-epoxy compositions including the reaction product of:

(a) a curing agent composition including the contact product of:
  (i) the benzylated Mannich base composition having at least one benzylated Mannich base compound having at least two nitrogen atoms, at least two active amine hydrogen atoms, and at least one benzyl group per molecule; and
  (ii) at least one multifunctional amine having two or more active amine hydrogens per molecule; and (b) an epoxy composition comprising at least one multifunctional epoxy resin.

Articles of manufacture produced from amine-epoxy compositions disclosed herein include, but are not limited to, adhesives, coatings, primers, sealants, curing compounds, construction products, flooring products, and composite products. Further, such coatings, primers, sealants, or curing compounds may be applied to metal or cementitious substrates.

Benzylated Mannich base compositions have excellent compatibility with epoxy resin, particularly with most common epoxy resins based on bisphenol A or bisphenol F as well as polyepoxy novolac resins. The benzyl group is aromatic in nature, thus enhances compatibility with epoxy resins that also contain aromatic moieties. The mix of curing agent and epoxy resin often requires no "ripening time" for obtaining contact products with high gloss and clarity. Ripening time or incubation time or induction time is defined as the time between mixing epoxy resin with amine and applying the product onto the target substrate. It could also be defined as the time required for the mix to become clear. Furthermore, the benzylated Mannich base compositions also provide faster amine-epoxy reaction rate, and relatively low viscosity. These unique properties provide the advantages of lower tendency to carbamate, shorter time for coatings to dry, and reduced or eliminated amounts of solvent or alkylphenol.

In another exemplary embodiment, there are provided epoxy systems or compositions, including the contact product of the above benzylated Mannich base composition reaction product, and an epoxy resin.

Other features and advantages of the present invention will be apparent from the following more detailed description of the preferred embodiment, taken in conjunction with the accompanying drawings which illustrate, by way of example, the principles of the invention.

DETAILED DESCRIPTION OF THE INVENTION

The present invention discloses benzylated Mannich base compounds, curing agent compositions and methods of making such compounds and compositions. These curing agent compositions may be used to cure, harden, and/or crosslink an epoxy resin. The present invention comprises benzylated Mannich base composition comprising at least one benzylated Mannich base compound having at least two nitrogen atoms, at least two active amine hydrogen atoms and at least one benzyl group per molecule.

The benzylated Mannich base composition comprising at least one benzylated Mannich base compound having at least two nitrogen atoms, at least two active amine hydrogen atoms and at least one benzyl group per molecule comprise the reaction product of an amine-exchange reaction by reacting:

(a) a substituted phenolic compound (Mannich base) having at least one substituent of formula (I):

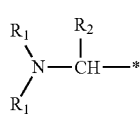

(I)

wherein $R_1$ is each independently a linear or branched alkyl group having 1 to 4 carbon atoms, and $R_2$ is hydrogen, methyl, ethyl or phenyl; with (b) a benzylated polyalkylene polyamine having at least two nitrogen atoms, at least two active amine hydrogen atoms and at least one benzyl group of formula (II):

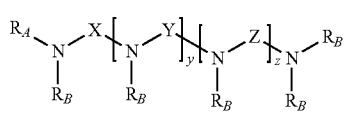

(II)

wherein $R_A$ is substituted or unsubstituted benzyl; $R_B$ is each independently $R_A$, or a hydrogen atom, or a group selected from $C_1$-$C_{16}$ linear, cyclic, and branched alkyl, alkenyl, and alkaryl groups; X, Y, and Z are independently selected from $C_2$-$C_{10}$ alkylene, and cycloalkylene groups; y is an integer from 0 to 7, and z is an integer from 0 or 4; and (c) optionally, a multifunctional amine having at least two nitrogen atoms, at least two active amine hydrogen atoms per molecule.

The benzylated polyalkylene polyamine having at least two nitrogen atoms, at least two active amine hydrogen atoms and at least one benzyl group is disclosed in U.S. Pat. Nos. 8,147,964, 8,143,331, the disclosure of which is incorporated by reference herein.

Suitable X, Y, and Z in formula (II) are ethylene, propylene, butylene, hexylene, cycylohexyldimethylene, and cyclohexalene groups, y and z are integers from 0 to 4. More suitable X, Y, and Z are ethylene, propylene, and cycylohexyldimethylene, and y and z are integers from 0 to 3.

The substituted phenolic compounds (Mannich bases) are preferably low molecular weight di-alkylaminomethyl-substituted phenols, ortho-, meta- and para-cresols, cardanol, the isomeric xylenols, para-tert-butylphenol, para-nonylphenol, alpha-naphthol, beta-naphthol, diphenols or polyphenols, such as resorcinol, hydroquinone, 4,4'-dihydroxydiphenyl, 4,4'-dihydroxydiphenyl ether, 4,4'-dihydroxydiphenylsulfone, 4,4'-dihydroxydiphenylmethane, bisphenol A, as well as the condensation products of phenol and formaldehyde known as novolaks. Preference is given to di-$C_1$-$C_4$-alkylaminomethyl-substituted phenols, cardanol, and cresols, especially substituted phenol and cardanol.

$R_1$, is each independently linear or branched alkyl group having 1 to 4 carbon atoms, and $R_2$ is hydrogen, methyl, ethyl or phenyl. In suitable examples, $R_1$ is each independently methyl or ethyl, and $R_2$ is hydrogen, methyl, or ethyl. In more suitable examples $R_1$ is methyl, and $R_2$ is hydrogen.

The substituent of formula (I) of the substituted phenolic compound, also known as Mannich base, is preferably di-$C_1$-$C_4$-alkylaminomethyl, for example, dimethylaminomethyl, ethylmethylaminomethyl, and diethylaminomethyl, especially dimethylaminomethyl. It should be desirably possible for the low molecular weight dialkylamine, for example, dimethylamine liberated in the amine exchange reaction, to be readily removed from the reaction mixture based on its low boiling point. The removal of the liberated dialkylamine shifts the reaction equilibrium to the product side and drives the exchange reaction to desired degree of conversion.

The substituted phenolic compounds, also known as Mannich bases, are obtained by reacting a phenolic compound with formaldehyde, acetaldehyde, propionaldehyde, butylaldehyde, or benzaldehyde, and the appropriate amine. An example of the aldehyde includes, but is not limited to, formaldehyde. The amine is selected from a primary or a secondary amine, preferably a secondary amine, especially a secondary monoamine. The secondary amine may be selected from dimethylamine, diethylamine, dipropylamine, dibutylamine, piperidine, pyrolidine, morpholine, and methylpiperazine, preferably dimethylamine.

The molar amount of formaldehyde and amine used per mol of the phenol employed depends on the number of substitutable groups in the phenol. For example, in phenol itself it is 3, in p-cresol 2, cardanol 3, in bisphenol A 4, in para-tertiarybutylphenol 2, and in novolacs up to 10 and more.

The Mannich bases which are preferred for the present invention are the reaction products of phenol, t-butylphenol, nonylphenol, cardanol, or cresol with formaldehyde and dimethylamine, having 1 to 3 substitutents of formula (I), in this case dimethylaminomethyl groups.

Mannich bases used may be selected from the following formulae 1 to 21, wherein $R_1$ and $R_2$ are defined for formula (I). In practice, a mixture of those compounds may also be used. Preferably, Mannich bases are selected from formulae 1, 2a, 3, 4, 5, 6, 9, 15, 16a, 16b, 18, 19, 20, and 21. More preferably, Mannich bases are selected from formulae 1, 2a, 3, 5, 6, 15, 16b, 18, 19, and 21, especially formulae 2a, 3, 5, 15, 16b, 18, 19, and 21. And in the preferred formulae, $R_1$ is independently methyl or ethyl, especially methyl.
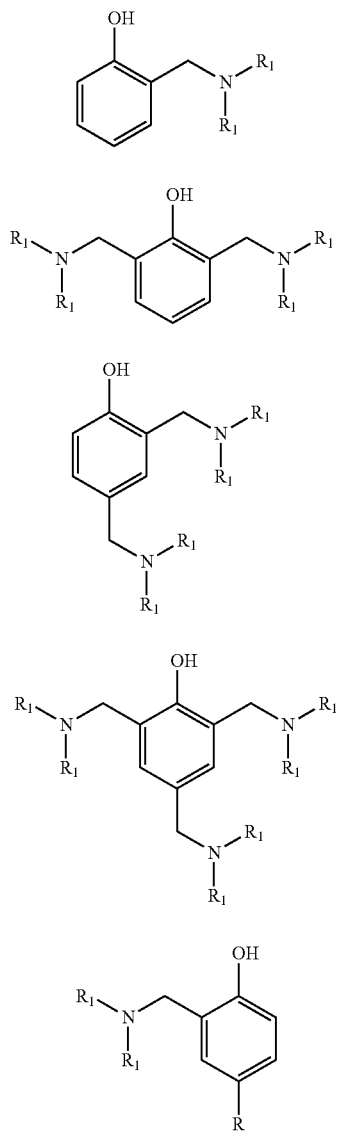
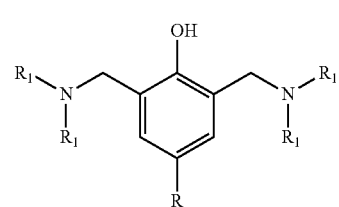
R = CH₃, t-butyl, C₉H₁₉
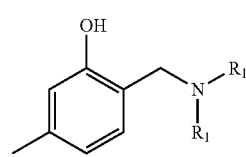
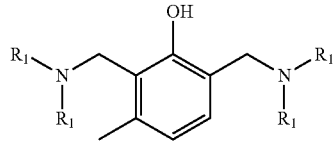
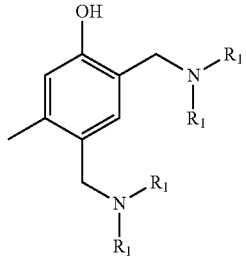
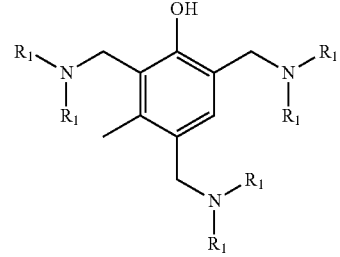
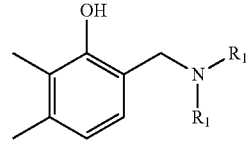
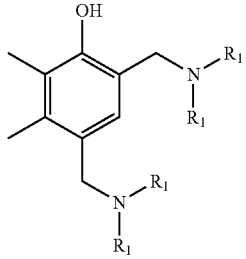
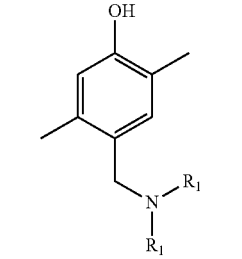
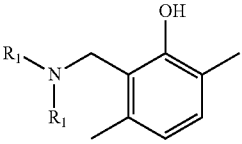

| | |
|---|---|
| 12 (structure: phenol with OH, two methyl groups, and two CH2-NR1R1 substituents) | 16a (structure: phenol with OH, two CH2-NR1R1 groups, and C15H27) |
| 13a (structure: phenol with OH, two methyl groups, one CH2-NR1R1) | 16b (structure: phenol with OH, two CH2-NR1R1 groups, and C15H27) |
| 13b (structure: phenol with OH, two methyl groups, one CH2-NR1R1 at para) | 17 (structure: phenol with OH, three CH2-NR1R1 groups, and C15H27) |
| 13c (structure: phenol with OH, two methyl groups, two CH2-NR1R1 groups) | 18 (structure: phenol with OH, two R groups, one CH2-NR1R1) R = CH₃, t-butyl |
| 13d (structure: phenol with OH, one methyl, two CH2-NR1R1 groups) | |
| 14 (structure: phenol with OH, two methyl groups, three CH2-NR1R1 groups) | 19 (structure: phenol with OH, one CH2-NR1R1, two R groups) R = CH₃, t-butyl |
| 15 (structure: phenol with OH, C15H27 group, one CH2-NR1R1) | 20 (structure: phenol with OH, R group, one CH2-NR1R1) R = CH₃, t-butyl |

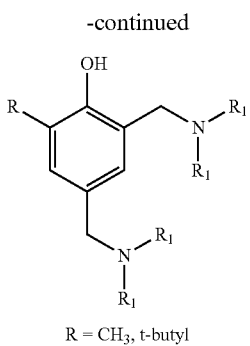

21

R = CH₃, t-butyl

The Mannich bases of formulae 1 to 21 are derived from the reaction of corresponding phenols with formaldehyde and the secondary amine $NHR_1R_1$. In the most preferred formulae 2a, 3, 5, 15, 16b, 18, 19, and 21, the secondary amine is dimethylamine $NH(CH_3)_2$. A common commercially available Mannich base is Ancamine® K54 from Air Products and Chemicals, Inc. It is a mixture of about 90-95 wt % of formula 3 and about 5-10 wt % of formula 2a wherein $R_1=CH_3$.

In accordance with the present invention, the Mannich bases described above are reacted, by means of an amine exchange reaction, with a benzylated polyalkylene polyamine of formula (II) having at least two nitrogen atoms, at least two active amine hydrogen atoms and at least one benzyl group. The reaction products are the benzylated Mannich bases of the present invention. Depending on the structure of the Mannich bases, including but not limited to, those of formulae 1 to 21, one or more than one $NR_1R_1$ substituent may be exchanged with benzylated polyalkylene polyamine. For example, in formula 3, and when $R_1$ is methyl, only one dimethylaminomethyl substituent or only two of the substituents, and at most three, may, as desired, be brought to reaction, the unreacted dimethylaminomethyl substituent(s) remaining unchanged on the phenolic nucleus. Upon continuation of the reaction, dimerization and further reaction to linear and branched oligomeric forms occur. The degree of dimerization and oligomer formation influences the viscosity of the benzylated Mannich base of the present invention.

The amine exchange reaction of Mannich base with benzylated polyalkylene polyamine of formula (II) is preferably carried out using a Mannich base of formulae 1, 2a, 3, 4, 5, 6, 9, 15, 16a, 16b, 18, 19, 20, or 21, and more preferably, of formulae 1, 2a, 3, 5, 6, 15, 16b, 18, 19, or 21, and of especially formulae 2a, 3, 5, 15, 16b, 18, 19, or 21. According to the present invention, the amine exchange reaction is carried out until, on average, at least 10 mol %, or at least 20 mol %, or at least 30 mol %, or at least 40 mol %, or at least 50 mol % of substituent of formula (I) amine-exchange with benzylated polyalkylene polyamine of formula (II). Or the amine-exchange reaction is carried out until, on average, at least one substituent of formula (I) per molecule of the Mannich base has reacted with benzylated polyalkylene polyamine of formula (II) or a mixture of benzylated polyalkylene polyamine of formula (II) with multifunctional amines having at least two nitrogen atoms, at least two active amine hydrogen atoms per molecule. The amine-exchange reaction is preferably carried out until at least 10% and a maximum of 100% on molar base, or at least 20% to 90%, or from 30% to 85%, or from 40% to 85%, or from 45% to 85%, or from 50% to 80%, of the di-$C_1$-$C_4$ alkylamino substituents of formula (I) present have reacted with benzylated polyalkylene polyamine of formula (II), or mixture of benzylated polyalkylene polyamine for formula (II) with multifunctional amines. The degree of reaction is measured, for example, by measuring the amine liberated by the Mannich base. An optimum balance between monomeric, dimeric, and oligomeric compounds is generally achieved at a degree of reaction in the range from 45% to 90% of the di-$C_1$-$C_4$ alkyl-amino substituents. This balance also manifests itself on measurement of the viscosity of the composition obtained, and the viscosity is in the range from 50 centipoise to 250,000 centipoise at 25° C., and preferably in the range from 100 centipoise to 150,000 centipoise, or from 100 to 100,000 centipoise, or from 100 to 80,000 centipoise, or from 100 to 50,000 centipoise, or from 100 to 30,000 centipoise, or from 100 to 25,000 centipoise, or from 100 to 15,000 centipoise, or from 100 to 10,000 centipoise, or from 100 to 8,000 centipoise, or from 100 to 6,000 centipoise, or from 100 to 5,000 centipoise, or from 100 to 3,000 centipoise, or from 500 centipoise to 150,000 centipoise, or from 500 to 100,000 centipoise, or from 500 to 80,000 centipoise, or from 500 to 50,000 centipoise, or from 500 to 30,000 centipoise, or from 500 to 25,000 centipoise, or from 500 to 15,000 centipoise, or from 500 to 10,000 centipoise, or from 500 to 8,000 centipoise, or from 1,000 centipoise to 150,000 centipoise, or from 1,000 to 100,000 centipoise, or from 1,000 to 80,000 centipoise, or from 1,000 to 50,000 centipoise, or from 1,000 to 30,000 centipoise, or from 1,000 to 25,000 centipoise, or from 1,000 to 15,000 centipoise, or from 1,000 to 10,000 centipoise at 25° C.

When the Mannich base is mono-substituted, such as formulae 1, 4, 6, 9, 11a, 11b, 13a, 13b, 15, 18, 19, or 20, and is used as starting material, the amine-exchange reaction is carried out until practically all the dialkylamino substituents or dimethylamino substituents present have reacted with benzylated polyalkylene polyamine of formula (II) or the mixture of benzylated polyalkylene polyamine of formula (II) with other multifunctional amines.

In one embodiment, the benzylated Mannich base compositions comprising the reaction product of a Mannich base having at least one substituent of formula (I) with a benzylated polyalkylene polyamine of formula (II) and, optionally, a multifunctional amine, by means of an amine-exchange reaction, have on average, per molecule, at least one substituent of formula (IIa):

(IIa)

wherein Formula (II) is attached to the carbon atom via any nitrogen atom of the Formula (II).

The amine-exchange reaction of the Mannich base with benzylated polyalkylene polyamines of formula (II) may optionally include other multifunctional amines in the exchange reaction, wherein the multifunctional amines are not the benzylated polyalkylene polyamines of formula (II), and have at least two nitrogen atoms, and at least two active amine hydrogen atoms per molecule. Specifically, the amine-exchange reaction takes place between the Mannich base and the mixture of benzylated polyalkylene polyamines of formula (II) and the multifunctional amines having at least two nitrogen atoms, and at least two active amine hydrogen atoms per molecule. Or the amine-exchange reaction takes place sequentially, reacting the Mannich base with benzylated polyalkylene polyamines of formula (II) first, followed by further reaction with the multifunctional amines, or the reaction sequence may be reversed. In another words, benzylated polyalkylene polyamines of formula (II) and other multifunctional amines co-exchange with Mannich base. The additional benefits of co-exchange include, but are not limited to, further reduced viscosity, further improved cure speed and mechanical properties, and other desired attributes. Further reduced viscosity is illustrated in inventive examples.

The multifunctional amines having at least two nitrogen atoms, and at least two active amine hydrogen atoms per molecule that are within the scope of the present invention include, but are not limited to, at least one member selected from the group consisting of an aliphatic amine, a polyether amine, a cycloaliphatic amine, an aromatic amine, a heterocyclic amine, an arylaliphatic amine, amidoamines, polyamides. The molar ratio of benzylated polyalkylene polyamines and the multifunctional amines varies, from about 95:5 to about 5:95, or from about 90:10 to about 10:90, or from about 75:25 to about 25:75, or from about 70:30 to about 30:70, or from about 60:40 to about 10:90, or from about 90:10 to about 50:50, or from about 90:10 to about 25:75, or from about 90:10 to about 40:60, or from about 90:10 to about 60:40, or from about 90:10 to about 40:60. Examples of the multifunctional amines are listed below.

The multifunctional amines that may be used with benzylated polyalkylene polyamines for the amine-exchange reaction with the Mannich base may comprise at least one member selected from aliphatic polyamines, cycloaliphatic polyamines, arylaliphatic polyamines, aromatic polyamines, and polyether amines, Mannich base derivative of an aliphatic amine, a cycloaliphatic amine, or an aromatic amine, polyamide and amidoamine derivative of an aliphatic amine, a cycloaliphatic amine, or an aromatic amine, amine adduct derivatives of an aliphatic amine, a cycloaliphatic amine, or an aromatic amine, or any combination thereof.

Exemplary aliphatic multifunctional amines having at least two nitrogen atoms, at least two active amine hydrogen atoms per molecule that may be used with benzylated polyalkylene polyamines for the amine-exchange reaction with the Mannich base may comprise at least one member selected from ethylene diamine (EDA), diethylenetriamine (DETA), triethylenetetramine (TETA), tetraethylenepentamine (TEPA), pentaethylenehexamine (PEHA), and the like), aminopropylated ethylenediamines (N-3-aminopropyl ethylenediamine (N3), N,N'-bis(3-aminopropyl) ethylenediamine (N4), N,N,N'-tris(3-aminopropyl) ethylenediamine (N5), N-3-aminopropyl diethylenetriamine (N4); N-3-aminopropyl-[N'-3-[N-3-aminopropyl]aminopropyl]diethylenetriamine (N6); N,N'-bis(3-aminopropyl)diethylenetriamine (N5); N,N-bis(3-aminopropyl)diethylenetriamine (N5); N,N,N'-tris(3-aminopropyl)diethylenetriamine (N6); N,N',N"-tris(3-aminopropyl)diethylenetriamine (N6); N,N,N',N'-tetrakis(3-aminopropyl)diethylenetriamine (N7); N,N-bis(3-aminopropyl)-[N'-3-[N-3-aminopropyl]aminopropyl]-[N'-3-aminopropyl]diethylenetriamine (N8); N-3-aminopropyl-[N'-3-[N-3-aminopropyl]aminopropyl]-[N'-3-aminopropyl]diethylenetriamine (N7); polypropyleneamines and aminopropylated propylenediamines (propylenediamine, dipropylenetriamine, tripropylenetetramine, N,N,N'-tris(3-aminopropyl)-1,3-diaminopropane, and the like), other aminopropylated amines (dimethylaminopropylamine (DMAPA), 3-dimethylaminopropyl propylene diamine (DMAPAPA), 3-aminopropyl propylene diamine (APCHA), bis(dimethylaminopropyl) amine (available from Aldrich, or as PolyCat® 15 from Air Products and Chemicals, Inc.), N-bis(3-aminopropyl)methylamine (Available from TCI America, or as PolyCat® 23 from Air Products and Chemicals, Inc.), 3,3,5-trimethyl-1,6-hexanediamine, 2-methyl-1,5-pentanediamine (commercially available as Dytek®-A), 1,6-hexanediamine (HMDA), and any combination thereof.

Particularly suitable aliphatic polyamines include at least one of DETA, TETA, TEPA, N3,N4,N5, 3,3,5-trimethyl-1,6-hexanediamine, DMAPA, DMAPAPA, APCHA, bis(dimethylaminopropyl)amine (PolyCat® 15), N-bis(3-aminopropyl)methylamine (PolyCat® 23), and any combination thereof.

The polyether multifunctional amines that may be used with benzylated polyalkylene polyamines for the amine-exchange reaction with the Mannich base include at least one member selected from the group consisting of poly(alkylene oxide) monoamines, diamines and triamines. Exemplary polyether amines include poly(ethylene oxide), poly(propylene oxide) and poly(tetramethylene oxide) monoamines, diamines and triamine. Poly(propylene oxide) monoamines, diamines and triamines useful in the present invention are commercially available under the Jeffamine® trademark from Huntsman Corporation. Illustrative examples include, but are not limited to, at least one of poly(ethylene glycol-block-propylene glycol) (2-amino-2-methyl) methyl ether (available as Jeffamine® M-600, Jeffamine® M-1000, Jeffamine® M-2005, and Jeffamine® M-2070), poly(ethylene glycol-block-propylene glycol) bis (2-amino-2-methyl) ether (available as Jeffamine® ED600, ED900, and ED 2001), tri(2-amiono-2-methylethyl) trimethylolpropane ether (available as Jeffamine® T-403), tri(2-amiono-poly(propylene oxide) glycerine ether (available as Jeffamine® T-5000), bis(3-aminopropyl) polypropylene glycol ether (Jeffamine® D230, D400, D2000, and D4000), and any combination thereof. Poly(ethylene oxide) monoamines, diamines and triamines include, but are not limited to, at least one of triethylene glycol diamine (available as Jeffamine® XTJ 504), bis(3-aminopropyl) diethylene glycol ether (available as Ancamine® 1922A), di(2-aminopropylated)diethylene glycol (also referred to as bis(2-amino-2-methylethyl) diethylene glycol ether, available as Jeffamine® XTJ-511), poly(ethylene oxide) methyl (3-aminopropyl) ether, poly(ethylene glycol) diamine (available as Jeffamine® XTJ-512), poly(ethylene oxide) bis(3-amino-propyl) ether, and any combination thereof. Poly (tetramethylene oxide) monoamines, diamines and triamines include, but are not limited to, at least one of bis(3-aminopropyl)polytetrahydrofuran (Mn 350), bis(3-aminopropyl) polytetrahydrofuran (Mn 750), poly(propylene oxide-block-tetramethylene oxide) bis(2-amino-2-methylethyl) ether (available as Jeffamine® XTJ-533, and XTJ-536), and any combination thereof.

Particularly suitable polyether multifunctional amines include at least one of triethylene glycol diamine (available as Jeffamine® XTJ 504), poly(ethylene glycol-block-propylene glycol) bis(2-amino-2-methyl) ether (available as Jeffamine® ED600, ED900, and ED 2001), tri(2-amiono-2-methylethyl) trimethylolpropane ether (available as Jeffamine® T-403), bis(3-aminopropyl) polypropylene glycol ether (Jeffamine® D230, D400, D2000, and D4000, bis(3-aminopropyl) diethylene glycol ether (available as Ancamine® 1922A), bis(2-amino-2-methylethyl) diethylene glycol ether (available as Jeffamine® XTJ-511), poly(ethylene oxide) methyl (3-aminopropyl) ether, poly(ethylene glycol) diamine (available as Jeffamine® XTJ-512), poly(ethylene oxide) bis(3-amino-propyl) ether, and bis(3-aminopropyl) polytetrahydrofuran, and any combination thereof.

Cycloaliphatic multifunctional amines that may be used with benzylated polyalkylene polyamines for the amine-exchange reaction with the Mannich base include, but are not limited to, at least one of 1,2-diaminocyclohexane, 1,3-diaminocyclohexane, 1,4-diaminocyclohexane, hydrogenated ortho-toluenediamine, hydrogenated meta-toluenediamine, hydrogenated metaxylylene diamine (referred to as 1, 3-bis(aminomethyl)cyclohexane, or 1,3-BAC), isophorone diamine (IPDA), norbornane diamines, 3,3'-dimethyl-4,4"-diaminodicyclohexyl methane, di(aminocyclohexyl)methane (including various isomers, such as up to about 5-wt. % 2,4-(diaminocyclohexyl)methane and at least about 95-wt. % 4,4'-(diaminocyclohexyl)methane (available as Amicure PACM from Air Products and Chemicals, Inc.)), 1,3-di(aminocyclohexyl)propane, 1-cyclohexylamino-3-aminopropane, di(aminocyclohexyl)sulfone, a mixture of methylene bridged poly(cyclohexyl-aromatic)amines, and the like, and combinations thereof. Particularly suitable cycloaliphaic polyamines include 4,4'-di(aminocyclohexyl) methane, isophorone diamine (IPDA), norbornane diamines, 1, 3-bis(aminomethyl)cyclohexane, 1,2-diaminocyclohexane, and 1-cyclohexylamino-3-aminopropane.

Aromatic multifunctional amines that may be used with benzylated polyalkylene polyamines for the amine-exchange reaction with the Mannich base include at least one of m-phenylenediamine, p-phenylenediamine diaminophenylmethane (DDM), tri(aminoethyl)benzene, tri(aminobutyl)naphthalene, toluene diamine (2-methy-p-phenylene diamine), diethyl toluene diamine, diaminodiphenylsulfone (DDS), and combinations thereof. The mixture of methylene bridged poly(cyclohexyl-aromatic)amines is abbreviated as either MBPCAA or MPCA, and is described in U.S. Pat. No. 5,280,091, which is incorporated herein by reference in its entirety. In one aspect of the present invention, the polyamine is a mixture of methylene bridged poly(cyclohexyl-aromatic)amines (MPCA).

Heterocyclic multifunctional amines that may be used with benzylated polyalkylene polyamines for the amine-exchange reaction with the Mannich base may comprise at least one member selected from N-aminoethylpiperazine (NAEP), 3,9-bis(3-aminopropyl)2,4,8,10-tetraoxaspiro (5,5) undecane, piperazine, 4,4'-trimethylenedipiperidine, 1,4-bis (3-aminopropyl)piperazine, 2,5-dimethylpiperazine, 2,6-dimethylpiperazine, 2-methylpiperazine, homopiperazine, and combinations thereof.

Arylaliphatic multifunctional amines that may be used with benzylated polyalkylene polyamines for the amine-exchange reaction with the Mannich base include examples, such as at least one of m-xylylenediamine (mXDA), p-xylylenediamine, di(aminoethyl)benzene, tri(aminoethyl)benzene, tri(aminobutyl)naphthalene, and combinations thereof.

The multifunctional amines may also include Mannich base polyamines derived from the reaction of the above-described aliphatic amines, cycloaliphatic amines, polyether amines, or aromatic amines with phenol or a substituted phenol and formaldehyde. An exemplary substituted phenol used to make Mannich bases with utility in the present invention is cardanol, which is obtained from cashew nut shell liquid. Alternatively, Mannich bases may be prepared by an exchange reaction of a multifunctional amine with at least one tertiary amine containing a Mannich base, such as 2,4,6-tris(N, N-dimethylaminomethyl) phenol (commercially available as Ancamine® K-54 from Air Products and Chemicals, Inc.) or bis(N,N-dimethylaminomethyl)phenol.

The multifunctional amines may also include amine-epoxy adducts prepared by the reaction of an aliphatic amine, a cycloaliphatic amine, a heterocyclic amine, a polyether amine, or an aromatic amine with an epoxy resin. This amine-epoxy adduct preparation is a common practice well known to those skilled in the art, and generally referred to as "adduction". By adducting with difunctional and monofunctional epoxy resins, it is possible to improve the compatibility of the curing agent with epoxy resin and thereby reduce problems, such as blush, carbamate and exudation, as described above, and to increase pot life. Particularly useful epoxy resins for adduction include at least one of the diglycidyl ethers of bisphenol-A and bisphenol-F, the advanced diglycidyl ethers of bisphenol-A and bisphenol A, styrene oxide, cyclohexene oxide, and the glycidyl ethers of phenol, the cresols, tert-butylphenol and other alkyl phenols, butanol, 2-ethylhexanol, and C8 to C14 alcohols and the like, and combinations thereof.

The multifunctional amines may also include amidoamines. Amidoamines are derived from a monobasic carboxylic acid and a polyamine, such as an aliphatic amine, a cycloaliphatic amine, a heterocyclic amine, or an aromatic amine. The monobasic carboxylic acids are usually at least one of the C16, C18, C19 type fatty acids derived from fats and oils, particularly from soya, tall oil, ricinoleic acids, and combinations thereof. If desired, amidoamines may be modified by reacting a portion of the amine hydrogen with difunctional and monofunctional epoxy resins, such as those described above.

In one embodiment of the present invention, the aliphatic polyamines that may be used in the amine-exchange reaction of the Mannich base with benzylated polyalkylene polyamines are represented by formulae (III), (IV), and (V):

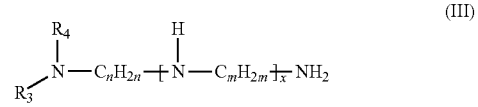

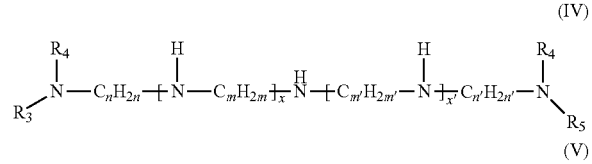

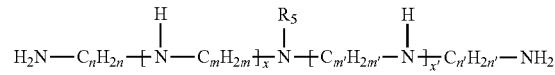

wherein $R_4$ and $R_3$ are each independently hydrogen atom, linear or branched alkyl group having 1 to 8 carbon atoms, cycloalkyl group having 4 to 10 carbon atoms, or together form a radical of formula $-(CH_2)_5-$, or $-(CH_2CH_2)-O-(CH_2CH_2)-$, and $R_4$ and $R_3$ cannot both be hydrogen atoms; $R_5$ is a linear or branched alkyl group having 1 to 8 carbon atoms, or cycloalkyl group having 4 to 10 carbon atoms; m, m', n and n' are integers from 2 to 5, and x and x' are integers from 0 to 3. Preferably, $R_4$ and $R_3$ are methyl, ethyl, or propyl; or when $R_4$ is a hydrogen, $R_3$ is a cyclohexyl; $R_5$ is an alkyl group having 1 to 4 carbon atoms, or cycloalkyl group having 6 to 8 carbon atoms; and specifically $R_4$ and $R_3$ are both methyl or ethyl; $R_5$ is methyl, ethyl, or cyclohexyl; n, n', m, and m' are 2, 3 or 4, and specifically, m, m', n and n' are 3, and x and x' are 0 or 1.

In one aspect, in formulae (III) and (IV), both $R_4$ and $R_3$ are independently linear or branched alkyl group having 1 to 8 carbon atoms, cycloalkyl group having 4 to 10 carbon atoms, and more preferably both $R_4$ and $R_3$ are methyl or ethyl, m, m', n and n' are 3, and x and x' are 0 or 1. In another aspect, in formula (III), $R_4$ is hydrogen, and $R_3$ is a cycloalkyl group having 4 to 10 carbon atoms, preferably a cyclohexyl group, m, and n are 3, and x and x' are 0 or 1. In yet another aspect, in formula (V), $R_5$ is methyl, ethyl, or cyclohexyl, m, m', n and n' are 3, and x and x' are 0 or 1, specifically, $R_5$ is methyl, m, m', n and n' are 3, and x and x' are 0.

In another embodiment, the benzylated Mannich base compositions include the reaction product of a Mannich base having at least one substituent of formula (I) with a benzylated polyalkylene polyamine of formula (II), and optionally a multifunctional amine, by means of an amine-exchange reaction, having on average, per molecule, less than one substituent of formula (IIIa)

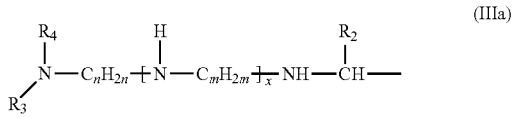

(IIIa)

wherein $R_4$ and $R_3$ are each independently linear or branched alkyl group having 1 to 8 carbon atoms, cycloalkyl group having 4 to 10 carbon atoms, or together form a radical of formula —$(CH_2)_5$—, or —$(CH_2CH_2)$—O—$(CH_2CH_2)$—, $R_2$ is hydrogen, methyl, ethyl or phenyl, m, and n are integers from 2 to 5, and x is an integer from 0 to 3.

The amine-exchange reaction takes place when reactants are combined in a reactor preferably in the absence of solvents and are heated to a temperature of from 50° C. to 190° C., preferably from 100° C. to 180° C. The reaction is monitored by the determination of the dialkylamine compound evolved. At the desired (partial) conversion stage, the reaction is stopped by lowering the temperature to about room temperature. The reaction product contains an average of more than two active amine hydrogen atoms per molecule.

In accordance with the present invention, a method of making a benzylated Mannich base composition is provided. This method includes reacting the following components via an amine-exchange reaction at a temperature from 50° C. to 190° C.:

(a) a substituted phenolic compound (Mannich base) having at least one substituent of formula (I):

(I)

wherein $R_1$ is each independently of linear or branched alkyl group having 1 to 4 carbon atoms, and $R_2$ is hydrogen, methyl, ethyl or phenyl; with (b) a benzylated polyalkylene polyamine having at least two nitrogen atoms, at least two active amine hydrogen atoms and at least one benzyl group of formula (II):

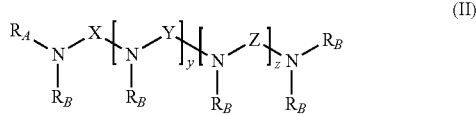

(II)

wherein $R_A$ is substituted or unsubstituted benzyl; $R_B$ is each independently $R_A$, or a hydrogen atom, or a group selected from $C_1$-$C_{16}$ linear, cyclic, and branched alkyl, alkenyl, and alkaryl groups; X, Y, and Z are independently selected from $C_2$-$C_{10}$ alkylene, and cycloalkylene groups; y is an integer from 0 to 7, and z is an integer 0 or 4; and (c) optionally, a multifunctional amine having at least two nitrogen atoms, and at least two active amine hydrogen atoms per molecule.

The method of making a benzylated Mannich base composition, according to the present invention, includes the process of carrying out an amine-exchange reaction to, on average, at least 10 mol %, or at least 20 mol %, or at least 30 mol %, or at least 40 mol %, or at least 50 mol % of substituent of formula (I) amine-exchanges with benzylated polyalkylene polyamine of formula (II). Alternatively, the method of making a benzylated Mannich base composition includes the process of carrying out an amine-exchange reaction to, on average, at least one substituent of formula (I) per molecule of the Mannich base has reacted with benzylated polyalkylene polyamine of formula (II) or a mixture of benzylated polyalkylene polyamine of formula (II) with multifunctional amines having at least two nitrogen atoms, at least two active amine hydrogen atoms per molecule. The amine exchange reaction is preferably carried out until at least 10% and a maximum of 100% on molar base, or at least 20% to 90%, or from 30% to 85%, or from 40% to 85%, or from 45% to 85%, or from 50% to 80%, of the di-$C_1$-$C_4$ alkylamino substituents of formula (I) present have reacted with benzylated polyalkylene polyamine of formula (II). Or the method of making a benzylated Mannich base composition comprises the process of carrying out an amine-exchange reaction to, on average on molar base, at least 10% to 100%, or at least 20% to 90%, or from 30% to 85%, or from 40% to 85%, or from 45% to 85%, or from 50% to 80%, of the di-$C_1$-$C_4$ alkylamino substituents for formula (I) present have reacted with benzylated polyalkylene polyamine of formula (II), or mixture of benzylated polyalkylene polyamine for formula (II) with multifunctional amines.

The benzylated polyalkylene polyamine compounds having at least two nitrogen atoms, at least two active amine hydrogen atoms and at least one benzyl group represented by formula (II) that are useful in producing the benzylated Mannich base of the present invention include, but are not limited to, benzylated polyethylene polyamines, benzylated polypropylene polyamines, benzylated polyethylene-polypropylene polyamines, and combinations thereof. Non-limiting examples of polyethylene polyamines include ethylene diamine (EDA), diethylenetriamine (DETA), triethylenetetramine (TETA), tetraethylenepentamine (TEPA), pentaethylenehexamine (PEHA), and other higher polyethylene polyamines. Suitable polypropylene polyamines include, but are not limited to, propylene diamine (PDA), dipropylenetriamine (DPTA), tripropylenetetramine, and other higher polypropylene polyamines. Other polyalkylene polyamines include N-3-aminopropyl ethylenediamine (N3, a compound that has 3 nitrogen atoms), N,N'-bis(3-aminopropyl) ethylenediamine (N4, a compound that has 4 nitrogen atoms), and N,N,N'-tris(3-aminopropyl) ethylenediamine (N5, a compound that has 5 nitrogen atoms), N-3-aminopropyl diethylenetriamine (N4); N-3-aminopropyl-[N'-3-[N-3-aminopropyl]aminopropyl]diethylenetriamine (N6, a compound that has 6 nitrogen atoms); N,N'-bis(3-aminopropyl)diethylenetriamine (N5); N,N-bis(3-aminopropyl)diethylenetriamine (N5); N,N,N'-tris(3-aminopropyl)diethylenetriamine (N6); N,N',N''-tris(3-aminopropyl)

diethylenetriamine (N6); N,N,N',N'-tetrakis(3-aminopropyl) diethylenetriamine (N7, a compound that has 7 nitrogen atoms); N,N-bis(3-aminopropyl)-[N'-3-[N-3-aminopropyl] aminopropyl]-[N'-3-aminopropyl]diethylenetriamine (N8, a compound that has 8 nitrogen atoms); and N-3-aminopropyl-[N'-3-[N-3-aminopropyl]aminopropyl]-[N'-3-aminopropyl]diethylenetriamine (N7). It will be recognized by those skilled in the art that polyethylene polyamines containing 4 or more nitrogen atoms are generally available as complex mixtures, most of which contain the same number of nitrogen atoms. Side products in these mixtures are often called congeners. For example, TETA contains not only linear TETA, but also tris-aminoethylamine, N,N'-bis-aminoethylpiperazine, and 2-aminoethylaminoethylpiperazine.

In one aspect of the present invention, the benzylated polyalkylene polyamine compound is benzylated EDA, benzylated DETA, benzylated TETA, benzylated TEPA, PEHA, benzylated propylene diamine (PDA), benzylated dipropylenetriamine (DPTA), benzylated tripropylenetetramine, benzylated N3, benzylated N4, benzylated N5, or any combination thereof. In another aspect, the benzylated polyalkylene polyamine compound is benzylated EDA, benzylated propylene diamine (PDA), benzylated DETA, or benzylated TETA, benzylated N3, benzylated N4, benzylated N5, a mixture of benzylated DETA and benzylated TETA, or a mixture of benzylated DETA, benzylated TETA, and benzylated N4. The mixture of benzylated polyalkylene polyamine may be prepared by blending each benzylated component, for example, blending benzylated DETA with benzylated TETA, or by benzylation reaction of a mixture of polyalkylene polyamine, for example, DETA and TETA. Preferably, the mixture of benzylated polyalkylene polyamine is prepared by benzylation reaction of a mixture of polyalkylene polyamine. For example, typical mixtures of benzylated DETA and benzylated TETA are benzylation reaction product of 1 part, by weight, of DETA to about 0.1 to about 1.1 parts, by weight, of TETA. In this and other aspects of the present invention, the mixtures of benzylated DETA and benzylated TETA may be the benzylation reaction product of 1 part, by weight, of DETA to about 0.1, about 0.2, about 0.3, about 0.4, about 0.5, about 0.6, about 0.7, about 0.8, about 0.9, about 1.0, or about 1.1 parts, by weight, of TETA. For example, DETA/TETA weight ratios of 70/30 and 50/50 are useful in the present invention to prepare the mixture of benzylated DETA and benzylated TETA, herein referred to as benzylated DETA/TETA.

The benzylation reaction to prepare benzylated polyalkylene polyamine compounds is the reductive amination reaction of benzaldehyde, including substituted and unsubstituted benzaldehydes, with a polyalkylene polyamine. Substituted benzaldehydes include, but are not limited to, compounds of the formula PhCHO in which the aromatic ring Ph is substituted with one or more of halogen atoms, C1-C4 alkyl, methoxy, ethoxy, amino, hydroxyl or cyano groups. In one aspect, the benzaldehyde compound is desirably benzaldehyde and in another aspect it is vanillin. In another aspect, the benzylated polyalkylene polyamine is prepared by the reductive amination reaction of a polyethylene polyamine with the benzaldehyde compound. The preferred embodiment comprises a benzylated polyethylene polyamine, benzylated N3, benzylated N4, and benzylated N5.

Procedures for the reductive amination of benzaldehyde are well known to those of skill in the art. Generally, these procedures involve condensing the benzaldehyde with the amine, then reducing the intermediate Schiff base. The reduction is typically conducted in the presence of a metal catalyst in a hydrogen-rich atmosphere at pressures above atmospheric pressure.

The benzylated polyalkylene polyamines of the present invention may also be prepared by the reaction of at least one polyalkylene polyamine compound with a benzyl halide. The benzyl halide may be a fluoride, chloride, bromide or iodide. The benzyl group may comprise unsubstituted benzyl or a substituted benzyl group. Substituted benzyl groups include, but are not limited to, radicals of the formula PhCH2- in which the aromatic ring Ph is substituted with one or more of halogen atoms, C1-C4 alkyl, methoxy, ethoxy, amino, hydroxyl or cyano groups. In one aspect, the benzyl group is desirably benzyl and in another aspect it is vanillyl.

Given the many possible locations on the polyalkylene polyamine compound where the benzyl group may replace a hydrogen atom, the product resulting from the reductive reaction of at least one polyalkylene polyamine compound and benzaldehyde compound or from the reaction with benzyl chloride is necessarily a mixture of many different species, where some of the $R_B$ groups are hydrogen or benzyl groups. Which and how many of the "R" groups are converted from hydrogen to benzyl groups depends on many factors, among those being the reaction conditions, catalyst selection, reactants ratio, choice of reactant (specific halide compound or benzaldehyde compound), and the like. For example, using a benzaldehyde compound as the reactant in a molar reactant ratio of benzaldehyde to the polyalkylene polyamine compound of between about 1:1 to about 2:1, the major component of the reaction product is where $R_A$ is benzyl, $R_B$ on the terminal nitrogen atom is benzyl or a hydrogen atom, and $R_B$ on the internal nitrogen atoms are hydrogen atoms.

The degree of benzylation depends on the equivalent ratio of benzaldehyde to reactive amine hydrogens in the polyalkylene polyamine in the reductive amination reaction, or the equivalent ratio of benzyl halide to reactive amine hydrogens in polyalkylene. Thus, in one aspect of the invention, the curing agent composition comprises a benzylated polyalkylene polyamine component comprising polyamine molecules having one, or two, or three, or four or more benzyl groups, or any combination thereof. For example, in one embodiment, benzylated EDA contains at least 90%, by weight, of mono-benzylated EDA. In another aspect, such benzylated polyalkylene polyamine component for the present invention comprises at least 5 wt % polyamines having at least two benzyl groups, i.e., having two or more benzyl groups. In other aspects of the invention, the benzylated polyalkylene polyamine component comprises 10 to 100 wt %, desirably 30 to 100 wt %, benzylated polyamines having two or more benzyl groups.

The polyalkylene polyamines of the present invention may also be prepared by aminopropylation of a benzylated amine. For example, benzyl amine is aminopropylated to generate monobenzylated propylene diamine. Monobenzylated propylene diamine may be further aminopropylated to produce higher monobenzylated polypropylene polyamine.

In one aspect of the present invention, the benzylated polyalkylene polyamine is polyethylene polyamine represented by formula (II):

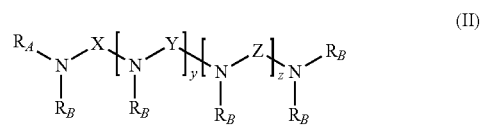

wherein X, Y, and Z are ethylene, y and z are integers of 0 to 4, $R_A$ is benzyl or vanillyl, and $R_B$ is hydrogen or benzyl.

In another aspect of the present invention, the benzylated polyalkylene polyamine is polyethylene-polypropylene polyamine represented by formula (II) wherein X, and Z are propylene, and Y is ethylene, y is 1 or 2, and z is 1, 2, 3 or 4, $R_A$ is benzyl or vanillyl, and $R_B$ is hydrogen or benzyl.

In yet another aspect of the present invention, the benzylated polyalkylene polyamine is polypropylene polyamine represented by formula (II) wherein X, Y and Z are propylene, y is 0, 1 or 2, and z is 1, 2, or 3, $R_A$ is benzyl or vanillyl, and $R_B$ is hydrogen or benzyl.

In another aspect of the present invention, the benzylated polyalkylene polyamine is polycyclohexyldimethylene-polypropylene polyamine represented by formula (II) wherein X, and Z are propylene, and Y is cyclohexyldimethylene, y is 1 or 2, and z is 1, 2, 3 or 4, $R_A$ is benzyl or vanillyl, and $R_B$ is hydrogen or benzyl.

The present invention also discloses benzylated Mannich base curing agent compositions and methods of making these compositions. A curing agent composition, in accordance with the present invention, may be used to cure, harden, and/or crosslink an epoxy resin. Such curing agent composition comprises a benzylated Mannich base composition having at least two nitrogen atoms, at least two active amine hydrogen atoms and at least one benzyl group per molecule.

The curing agent composition of the present invention comprising benzylated Mannich base has a relatively low viscosity, and the viscosity at 25° C. is in the range from 50 centipoise to 200,000 centipoise at 25° C. or in the range from 100 centipoise to 150,000 centipoise, or from 100 to 100,000 centipoise, or from 100 to 80,000 centipoise, or from 100 to 50,000 centipoise, or from 100 to 30,000 centipoise, or from 100 to 25,000 centipoise, or from 100 to 15,000 centipoise, or from 100 to 10,000 centipoise, or from 100 to 8,000 centipoise, or from 100 to 6,000 centipoise, or from 100 to 5,000 centipoise, or from 100 to 3,000 centipoise, or from 500 centipoise to 150,000 centipoise, or from 500 to 100,000 centipoise, or from 500 to 80,000 centipoise, or from 500 to 50,000 centipoise, or from 500 to 30,000 centipoise, or from 500 to 25,000 centipoise, or from 500 to 15,000 centipoise, or from 500 to 10,000 centipoise, or from 500 to 8,000 centipoise, or from 1,000 centipoise to 150,000 centipoise, or from 1,000 to 100,000 centipoise, or from 1,000 to 80,000 centipoise, or from 1,000 to 50,000 centipoise, or from 1,000 to 30,000 centipoise, or from 1,000 to 25,000 centipoise, or from 1,000 to 15,000 centipoise, or from 1,000 to 10,000 centipoise, or from 1,000 to 9,000 centipoise, or from 1,000 to 8,000 centipoise. The low viscosity provides the advantage of using less or no solvent to reduce viscosity for a coating composition, thus reduce VOC.

In another aspect, the present invention provides a curing agent composition comprising the contact product of:
  (a) at least one benzylated Mannich base composition including at least one benzylated Mannich base compound having at least two nitrogen atoms, at least two active amine hydrogen atoms and at least one benzyl group per molecule; and
  (b) at least one multifunctional amine having 2 or more active amine hydrogens.

The term "contact product" is used herein to describe compositions wherein the components are contacted together in any order, in any manner, and for any length of time. For example, the components may be contacted by blending or mixing. Further, contacting of any component may occur in the presence or absence of any other component of the compositions or formulations described herein. Still further, two or more of the components of the contact product may react to form other components composing the composition. Combining additional materials or components may be done by any method known to one of skill in the art.

Non-limiting examples of the multifunctional amines that are within the scope of the present invention include, but are not limited to, an aliphatic amine, a cycloaliphatic amine, an aromatic amine, a heterocyclic amine, an arylaliphatic amine, polyether amines, amidoamines, and polyamides. The multifunctional amines also include a Mannich base derivative of an aliphatic amine, a cycloaliphatic amine, an aromatic amine, a polyamide or an amidoamine; and an amine-epoxy adduct derivative of an aliphatic amine, a cycloaliphatic amine, an aromatic amine, a polyamide, or an amidoamine with a monoglycidyl ether of glycols or phenols, glycidyl ether of bisphenol A or bisphenol F or an epoxy novolac resin, and the like, and any combination thereof. Detailed examples of the multifunctional amines are listed previously.

More than one multifunctional amine may be used in the compositions of the present invention. For example, the at least one multifunctional amine may comprise an aliphatic amine and a Mannich base derivative of a cycloaliphatic amine. Also, the at least one multifunctional amine may comprise one aliphatic amine and one different aliphatic amine.

The curing agent compositions also may be further modified with monofunctional epoxies, such as, for example, phenyl glycidyl ether, o-cresyl glycidyl ether, p-tert-butylphenyl glycidyl ether, n-butyl glycidyl ether, and other similar glycidyl ethers or esters. Further, curing agent compositions disclosed herein may be blended with other commercially available curing agents. Such commercially available curing agents include, but are not limited to, solvent based, solvent free or water-based curing agents, which may be employed in a blend to target specific properties, such as cure rate, drying speed, hardness development, clarity, and gloss.

Generally, the curing agent composition has an amine hydrogen equivalent weight (AHEW) based on 100% solids from about 30 to about 500. Further, the curing agent composition may have an AHEW based on 100% solids from about 60 to about 400, or from about 80 to about 300, or from about 40 to about 200, or from about 55 to about 450, or from about 40 to about 150, or from about 70 to about 350, or from about 90 to about 250, or from about 100 to about 200.

Additionally, curing agent compositions described herein may also be solvent-based. Alternatively, in another aspect of the present invention, these compositions may further comprise at least one diluent, such as, for example, an organic solvent, or an organic or inorganic acid. Appropriate organic solvents are well known to those skilled in the art of amine formulation chemistry. Exemplary organic solvents suitable for use in the present invention include, but are not limited to, benzyl alcohol, butanol, toluene, xylene, methyl ethyl ketone, Dowanol solvents (from Dow Chemicals), and the like, or combinations thereof. Non-limiting examples of organic and inorganic acids are acetic acid, sulfamic acid, lactic acid, salicylic acid, sebacic acid, boric acid, phosphoric acid, p-toluene sulfonic acid, and the like, or combinations thereof. Such acids may increase the curing speed of the curing agent composition.

In accordance with the present invention, a method of making a curing agent composition is provided. This method comprises either using the benzylated Mannich base compositions as a curing agent or formulating with multifunctional amines having at least two nitrogen atoms and at least two active amine hydrogen atoms per molecule, catalysts, accelerators, non-reactive diluents, solvents and other additives necessary to achieve the required properties of the final curing agent composition.

The multifunctional amines that may be used to formulate with benzylated Mannich base compositions include, but are not limited to, at least one member selected from the group consisting of an aliphatic amine, a cycloaliphatic amine, an aromatic amine, a heterocyclic amine, an arylaliphatic amine, polyether amines, amidoamines, and polyamides, a Mannich base derivative, an amine-epoxy adduct, and any combination thereof. Detailed examples of the multifunctional amines are described above.

Curing agent compositions described herein may maintain single-phase uniformity for extended periods of time, which may be required for storage of the product and its subsequent use in its intended application. Additionally, if these compositions are substantially free of solvents, they may have substantially no VOCs, which is beneficial for environmental, health and safety issues, as will be appreciated by those skilled in the art.

The present invention also includes amine-epoxy compositions and the cured products produced therefrom. An amine-epoxy composition, in accordance with the present invention, comprises the reaction product of:

(a) a curing agent composition comprising the benzylated Mannich base composition comprising at least one benzylated Mannich base compound having at least two nitrogen atoms, at least two active amine hydrogen atoms, and at least one benzyl group per molecule; and (b) an epoxy composition comprising at least one multifunctional epoxy resin.

The present invention, in yet another embodiment, provides amine-epoxy compositions comprising the reaction product of:

(a) a curing agent composition comprising the contact product of:
  (i) the benzylated Mannich base composition comprising at least one benzylated Mannich base compound having at least two nitrogen atoms, at least two active amine hydrogen atoms, and at least one benzyl group per molecule, and
  (ii) at least one multifunctional amine having two or more active amine hydrogens per molecule; and (b) an epoxy composition comprising at least one multifunctional epoxy resin.

The present invention also includes articles of manufacture comprising an amine-epoxy composition as described above. Such articles may include, but are not limited to, an adhesive, a coating, a primer, a sealant, a curing compound, a construction product, a flooring product, a composite product, laminate, potting compounds, grouts, fillers, cementitious grouts, or self-leveling flooring. Additional components or additives may be used together with the compositions of the present invention to produce articles of manufacture. Further, such coatings, primers, sealants, curing compounds or grouts may be applied to metal or cementitious substrates.

The relative amount chosen for the epoxy composition versus that of the curing agent composition, may vary depending upon, for example, the end-use article, its desired properties, and the fabrication method and conditions used to produce the end-use article. For instance, in coating applications using certain amine-epoxy compositions, incorporating more epoxy resin relative to the amount of the curing agent composition may result in coatings which have increased drying time, but with increased hardness and improved appearance as measured by gloss. Amine-epoxy compositions, according to present invention, generally have stoichiometric ratios of epoxy groups in the epoxy composition to amine hydrogens in the curing agent composition ranging from about 1.5:1 to about 0.7:1. For example, such amine-epoxy compositions may have stoichiometric ratios of about 1.5:1, about 1.4:1, about 1.3:1, about 1.2:1, about 1.1:1, about 1:1, about 0.9:1, about 0.8:1, or about 0.7:1. In another aspect, the stoichiometric ratio ranges from about 1.4:1 to about 0.7:1, or from about 1.3:1 to about 0.7:1, or from about 1.2:1 to about 0.8:1, or from about 1.1:1 to about 0.9:1.

Amine-epoxy compositions of the present invention include the reaction product of a curing agent composition and an epoxy composition including at least one multifunctional epoxy resin. Multifunctional epoxy resin, as used herein, describes compounds containing 2 or more 1,2-epoxy groups per molecule.

The epoxy resin is selected from the group consisting of aromatic epoxy resin, alicyclic epoxy resin, aliphatic epoxy resin, glycidyl ester resin, thioglycidyl ether resin, N-glycidyl ether resin, and combinations thereof.

Aromatic epoxy resins suitable for use in the present invention include the glycidyl ethers of polyhydric phenols, including the glycidyl ethers of dihydric phenols. Illustrative examples include, but are not limited to, the glycidyl ethers of resorcinol, hydroquinone, bis-(4-hydroxy-3,5-difluorophenyl)-methane, 1,1-bis-(4-hydroxyphenyl)-ethane, 2,2-bis-(4-hydroxy-3-methylphenyl)-propane, 2,2-bis-(4-hydroxy-3,5-dichlorophenyl) propane, 2,2-bis-(4-hydroxyphenyl)-propane (commercially known as bisphenol A), bis-(4-hydroxyphenyl)-methane (commercially known as bisphenol F, and which may contain varying amounts of 2-hydroxyphenyl isomers), and the like, or any combination thereof. Additionally, advanced dihydric phenols of the following structure also are useful in the present invention:

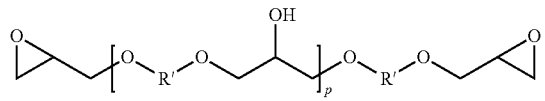

wherein R' is a divalent hydrocarbon radical of a dihydric phenol, such as those dihydric phenols listed above, and p is an average value between 0 and about 7. Materials according to this formula may be prepared by polymerizing mixtures of a dihydric phenol and epichlorohydrin, or by advancing a mixture of a diglycidyl ether of the dihydric phenol and the dihydric phenol. While in any given molecule the value of p is an integer, the materials are invariably mixtures which may be characterized by an average value of p which is not necessarily a whole number. Polymeric materials with an average value of p between 0 and about 7 may be used in one embodiment of the present invention.

In one embodiment of the present invention, the at least one multifunctional epoxy resin is a diglycidyl ether of bisphenol-A (DGEBA), an advanced or higher molecular weight version of DGEBA, a diglycidyl ether of bisphenol-F, a diglycidyl ether of novolac resin, or any combination thereof. Higher molecular weight versions or derivatives of DGEBA are prepared by the advancement process, where excess DGEBA is reacted with bisphenol-A to yield epoxy terminated products. The epoxy equivalent weights (EEW) for such products range from about 450 to about 3000 or more. Because these products are solid at room temperature, they are often referred to as solid epoxy resins.

In preferred embodiments, the at least one multifunctional epoxy resin is the diglycidyl ether of bisphenol-F or bisphenol-A represented by the following structure:

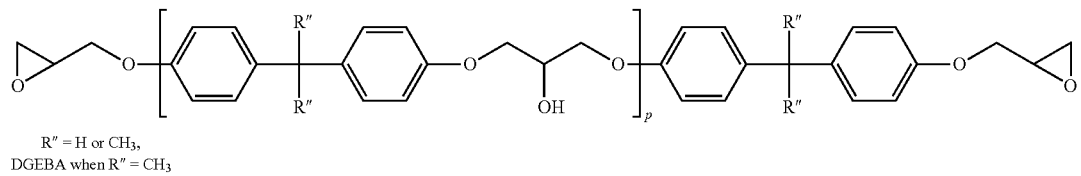

R″ = H or CH$_3$,
DGEBA when R″ = CH$_3$

DGEBA or advanced DGEBA resins are often used in coating formulations due to a combination of their low cost and generally high performance properties. Commercial grades of DGEBA having an EEW ranging from about 174 to about 250, and more commonly from about 185 to about 195, are readily available. At these low molecular weights, the epoxy resins are liquids and are often referred to as liquid epoxy resins. It is understood by those skilled in the art that most grades of liquid epoxy resin are slightly polymeric, since pure DGEBA has an EEW of about 174. Resins with EEWs between about 250 and about 450, also generally prepared by the advancement process, are referred to as semi-solid epoxy resins because they are a mixture of solid and liquid at room temperature. Generally, multifunctional resins with EEWs based on solids of about 160 to about 750 are useful in the present invention. In another embodiment, the multifunctional epoxy resin has an EEW in a range from about 170 to about 250.

Examples of alicyclic epoxy compounds include, but are not limited to, polyglycidyl ethers of polyols having at least one alicyclic ring, or compounds including cyclohexene oxide or cyclopentene oxide obtained by epoxidizing compounds including a cyclohexene ring or cyclopentene ring with an oxidizer. Some particular examples include, but are not limited to, hydrogenated bisphenol A diglycidyl ether; 3,4-epoxycyclohexylmethyl-3,4-epoxycyclohexyl carboxylate; 3,4-epoxy-1-methylcyclohexyl-3,4-epoxy-1-methylhexane carboxylate; 6-methyl-3,4-epoxycyclohexylmethyl-6-methyl-3,4-epoxycyclohexane carboxylate; 3,4-epoxy-3-methylcyclohexylmethyl-3,4-epoxy-3-methylcyclohexane carboxylate; 3,4-epoxy-5-methylcyclohexylmethyl-3,4-epoxy-5-methylcyclohexane carboxylate; bis(3,4-epoxycyclohexylmethyl)adipate; methylene-bis(3,4-epoxycyclohexane); 2,2-bis(3,4-epoxycyclohexyl)propane; dicyclopentadiene diepoxide; ethylene-bis(3,4-epoxycyclohexane carboxylate); dioctyl epoxyhexahydrophthalate; and di-2-ethylhexyl epoxyhexahydrophthalate.

Examples of aliphatic epoxy compounds include, but are not limited to, polyglycidyl ethers of aliphatic polyols or alkylene-oxide adducts thereof, polyglycidyl esters of aliphatic long-chain polybasic acids, homopolymers synthesized by vinyl-polymerizing glycidyl acrylate or glycidyl methacrylate, and copolymers synthesized by vinyl-polymerizing glycidyl acrylate or glycidyl methacrylate and other vinyl monomers. Some particular examples include, but are not limited to, glycidyl ethers of polyols, such as 1,4-butanediol diglycidyl ether; 1,6-hexanediol diglycidyl ether; a triglycidyl ether of glycerin; a triglycidyl ether of trimethylol propane; a tetraglycidyl ether of sorbitol; a hexaglycidyl ether of dipentaerythritol; a diglycidyl ether of polyethylene glycol; and a diglycidyl ether of polypropylene glycol; polyglycidyl ethers of polyether polyols obtained by adding one type, or two or more types, of alkylene oxide to aliphatic polyols, such as ethylene glycol, propylene glycol, trimethylol propane, and glycerin.

Glycidyl ester resins are obtained by reacting a polycarboxylic acid compound having at least two carboxyl acid groups in the molecule and epichlorohydrin. Examples of such polycarboxylic acids include aliphatic, cycloaliphatic, and aromatic polycarboxylic acids. Examples of aliphatic polycarboxylic acids include oxalic acid, succinic acid, glutaric acid, adipic acid, pimelic acid, sebacic acid, suberic acid, azelaic acid, or dimerised or trimerised linoleic acid. Cycloaliphatic polycarboxylic acids include tetrahydrophthalic acid, 4-methyltetrahydrophthalic acid, hexahydrophthalic acid or 4-methylhexahydrophthalic acid. And aromatic polycarboxylic acids include phthalic acid, isophthalic acid or terephthalic acid.

Thioglycidyl ether resins are derived from dithiols, for example, ethane-1,2-dithiol or bis(4-mercaptomethylphenyl) ether.

N-glycidyl resins are obtained by dehydrochlorination of the reaction products of epichlorohydrin with amines containing at least two amine hydrogen atoms. Such amines are, for example, aniline, n-butylamine, bis(4-aminophenyl) methane, m-xylylenediamine or bis(4-methylaminophenyl) methane. The N-glycidyl resins also include, however, triglycidyl isocyanurate, N,N'-diglycidyl derivatives of cycloalkylene ureas, e.g., ethylene urea or 1,3-propylene urea, and diglycidyl derivatives of hydantoins, e.g., 5,5-dimethylhydantoin.

For one or more of the embodiments, the resin component further includes a reactive diluent. Reactive diluents are compounds that participate in a chemical reaction with the hardener component during the curing process and become incorporated into the cured composition, and are generally monofunctional epoxides. Reactive diluents may also be used to vary the viscosity and/or cure properties of the curable compositions for various applications. For some applications, reactive diluents may impart a lower viscosity to influence flow properties, extend pot life and/or improve adhesion properties of the curable compositions. For example, the viscosity may be reduced to allow an increase in the level of pigment in a formulation or composition while still permitting easy application, or to allow the use of a higher molecular weight epoxy resin. Thus, it is within the scope of the present invention for the epoxy component, which comprises at least one multifunctional epoxy resin, to further comprise a monofunctional epoxide. Examples of monoepoxides include, but are not limited to, styrene oxide, cyclohexene oxide and the glycidyl ethers of phenol, cresols, tert-butylphenol, other alkyl phenols, butanol, 2-ethylhexanol, C4 to C14 alcohols, and the like, or combinations thereof. The multifunctional epoxy resin may also be present in a solution or emulsion, with the diluent being water, an organic solvent, or a mixture thereof. The amount of multifunctional epoxy resin may range from about 50% to 100%, about 50% to about 90%, about 60% to about 90%, about 70% to 90%, and in some cases about 80% to about 90%, by weight, of the epoxy component. For one or more of the embodiments, the reactive diluent is less than 60 wt % of a total weight of the resin component.

Particularly suitable multifunctional epoxy compounds are the diglycidyl ethers of bisphenol-A and bisphenol-F, the advanced diglycidyl ethers of bisphenol-A and bisphenol-F, and the epoxy novolac resins. The epoxy resin may be a single resin, or it may be a mixture of mutually compatible epoxy resins.

Compositions of the present invention may be used to produce various articles of manufacture. Depending on the requirements during the manufacturing of or for the end-use application of the article, various additives may be employed in the formulations and compositions to tailor specific properties. These additives include, but are not limited to, solvents (including water), accelerators, plasticizers, fillers, fibers, such as glass or carbon fibers, pigments, pigment dispersing agents, rheology modifiers, thixotropes, flow or leveling aids, surfactants, defoamers, biocides, or any combination thereof. It is understood that other mixtures or materials that are known in the art may be included in the compositions or formulations and are within the scope of the present invention.

The present invention also is directed to articles of manufacture comprising the compositions disclosed herein. For example, an article may comprise an amine-epoxy composition which comprises the reaction product of a curing agent composition and an epoxy composition. The curing agent composition may comprise the contact product of at least one multifunctional amine having 2 or more active amine hydrogens and the benzylated Mannich base. The epoxy composition may comprise at least one multifunctional epoxy resin. Optionally, various additives may be present in the compositions or formulations used to produce fabricated articles, dependent upon the desired properties. These additives may include, but are not limited to, solvents (including water), accelerators, plasticizers, fillers, fibers, such as glass or carbon fibers, pigments, pigment dispersing agents, rheology modifiers, thixotropes, flow or leveling aids, surfactants, defoamers, biocides, or any combination thereof.

Articles in accordance with the present invention include, but are not limited to, a coating, an adhesive, a construction product, a flooring product, or a composite product. Coatings based on these amine-epoxy compositions may be solvent-free or may contain diluents, such as water or organic solvents, as needed for the particular application. Coatings may contain various types and levels of pigments for use in paint and primer applications. Amine-epoxy coating compositions comprise a layer having a thickness ranging from 40 to 400 µm (micrometer), preferably 80 to 300 µm, more preferably 100 to 250 µm, for use in a protective coating applied onto metal substrates. In addition, for use in a flooring product or a construction product, coating compositions comprise a layer having a thickness ranging from 50 to 10,000 µm, depending on the type of product and the required end-properties. A coating product that delivers limited mechanical and chemical resistances comprises a layer having a thickness ranging from 50 to 500 µm, preferably 100 to 300 µm; whereas a coating product, such as, for example, a self-leveling floor that delivers high mechanical and chemical resistances comprises a layer having a thickness ranging from 1,000 to 10,000 µm, preferably 1,500 to 5,000 µm.

Various substrates are suitable for the application of coatings of this invention with proper surface preparation, as is well known to one of ordinary skill in the art. Such substrates include, but are not limited to, concrete and various types of metals and alloys, such as steel and aluminum. Coatings of the present invention are suitable for the painting or coating of large metal objects or cementitious substrates including ships, bridges, industrial plants and equipment, and floors.

Coatings, according to the present invention, may be applied by any number of techniques including spray, brush, roller, paint mitt, and the like. In order to apply very high solids content or 100% solids coatings of this invention, plural component spray application equipment may be used, in which the amine and epoxy components are mixed in the lines leading to the spray gun, in the spray gun itself, or by mixing the two components together as they leave the spray gun. Using this technique may alleviate limitations with regard to the pot life of the formulation, which typically decreases as both the amine reactivity and the solids content increases. Heated plural component equipment may be employed to reduce the viscosity of the components, thereby improving ease of application.

Construction and flooring applications include compositions comprising the amine-epoxy compositions of the present invention in combination with concrete or other materials commonly used in the construction industry. Applications of compositions of the present invention include, but are not limited to, its use as a primer, a deep penetrating primer, a coating, a curing compound, and/or a sealant for new or old concrete, such as referenced in ASTM C309-97, which is incorporated herein by reference. As a primer or a sealant, the amine-epoxy compositions, according to the present invention, may be applied to surfaces to improve adhesive bonding prior to the application of a coating. As it pertains to concrete and cementitious application, a coating is an agent used for application on a surface to create a protective or decorative layer or a coat. Crack injection and crack filling products also may be prepared from the compositions disclosed herein. Amine-epoxy compositions of the present invention may be mixed with cementitious materials, such as concrete mix, to form polymer or modified cements, tile grouts, and the like. Non-limiting examples of composite products or articles comprising amine-epoxy compositions disclosed herein include tennis rackets, skis, bike frames, airplane wings, glass fiber reinforced composites, and other molded products.

In a particular use of the curing agent composition of the present invention, coatings may be applied to various substrates, such as concrete and metal surfaces at low temperature, with fast cure speed and good coating appearance. This is especially important for top-coat application where good aesthetics is desired, and provides a solution to a long-standing challenge in the industry where fast low-temperature cure with good coating appearance remains to be overcome. With fast low-temperature cure speed, the time service or equipment is down may be shortened, or for outdoor applications, the work season may be extended in cold climates.

Fast epoxy curing agents enable an amine-cured epoxy coating cures in short period of time with high degree of cure. The cure speed of a coating is monitored by thin film set time (TFST) which measures the time period a coating dries. The thin film set time is categorized in 4 stages: phase 1, set to touch; phase 2, tack free: phase 3, dry hard; and phase 4, dry through. The phase 3 dry time is indicative of how fast a coating cures and dries. For a fast ambient cure coating, phase 3 dry time is less than 10 hours, or less than 8 hours, or preferred to be less than 6 hours, or less than 5 hours, or less than 4 hours. Low temperature cure typically refers to cure temperature below ambient temperature, 10° C. or 5° C., or 0° C. in some cases. For a fast low temperature cure, phase 3 dry time at 5° C. is less than 24 hours, or less than 20 hours, or less than 15 hours, or less than 12 hours, or less than 10 hours.

How well a coating cures is measured by the degree of cure. Degree of cure is often determined by using DSC (differential scanning calorimetry) technique which is well-known to those skilled in the art. A coating cured thoroughly will have a degree of cure at ambient temperature of at least 85%, or at least 90%, or at least 95% after 7 days, and at least 80%, or at least 85%, or at least 90% at 5° C. after 7 days.

Many of the fast low temperature epoxy curing agents may cure an epoxy resin fast. However due to poor compatibility of the epoxy resin and curing agents especially at low temperature of 10° C. or 5° C., there is phase separation between resin and curing agent and curing agent migrating to coating surface, resulting in poor coating appearance manifested as sticky and cloudy coatings. Good compatibility between epoxy resin and curing agent leads to clear glossy coating with good carbamation resistance and good coating appearance. The curing agent compositions of the present invention offer the combination of fast cure speed, good compatibility and high degree of cure.

EXAMPLES

The following Examples are provided to illustrate certain aspects or embodiments of the instant invention and shall not limit the scope of the claims appended hereto.

Synthesis Examples

Example 1: Synthesis of Mixture of N-3-aminopropyl ethylenediamine, N,N'-bis(3-aminopropyl)ethylenediamine, and N,N,N'-tris(3-aminopropyl)ethylenediamine (N4 amine)

Step 1: Synthesis of the Intermediate

To a 1-liter batch reactor was added 236 g (3.93 moles) of ethylenediamine and 5 g of water. The contents was heated to 60° C. To this mixture was added 417 g (7.86 moles) of acrylonitrile over 5 hours. Once the acrylonitrile addition was completed, the reactor temperature was maintained for an additional 1.5 hours.

Step 2: Hydrogenation of the Intermediate

A 1-liter batch reactor was charged with 100 g of isopropanol, 6.6 g of water and 7.5 g of Raney Co catalyst. The reactor was pressure cycled first with nitrogen and then with hydrogen to remove traces of entrained air. After pressure cycling, the reactor was filled with 5.5 MPa hydrogen and then heated to 120° C. Then 500 g of intermediate from the previous step was added to the reactor over 4 hours. During this time, reactor pressure was maintained at 5.5 MPa by supplying hydrogen to it from a 1-liter ballast tank. Once the addition was completed, the temperature was maintained at 120° C. for an additional hour to complete the hydrogenation. The reactor was cooled down to room temperature, and the product was filtered. The product was analyzed by area percent GC and it contained 6% N-3-aminopropyl ethylenediamine, 80% N,N'-bis(3-aminopropyl)ethylenediamine, and 11% N, N, N'-tris(3-aminopropyl)ethylenediamine and 2% N, N, N',N'-tetrakis(3-aminopropyl)ethylenediamine. The product produced by the above method of Example 1 has been hereinafter designated as N4 amine of Example 1.

Example 2: Synthesis of Benzylated Diethylenetriamine (DETA) at 1.2:1 Molar Ratio DETA (340.6 g, 3.24 moles) and 5 g of Pd/C catalyst were placed in a 1-liter autoclave batch reactor. The reactor was sealed and subsequently purged with nitrogen and then with hydrogen to remove any air from the reactor. Benzaldehyde (420.2 g, 3.96 moles) was added to the reactor over about 15 to 20 minutes. After the addition of the benzaldehyde was complete, the content of the reactor was stirred for an additional 15 minutes or until the reaction was complete, at which time the reaction exotherm began to subside. At this point, the reactor was pressurized to 0.8.2 MPa (120 psi) with hydrogen and the reactor was heated to 80° C. When the rate of hydrogen uptake slowed, the pressure was increased to 5.44 MPa (800 psi) and the temperature was increased to 120° C. The hydrogenation process continued until the rate of hydrogen uptake fell below 0.0034 MPa/min (0.5 psi/min). The total hydrogenation time was about 5 hours. The reactor was cooled to 60° C. and depressurized, and the reaction product was filtered to remove the catalyst. Water was removed using a rotary-evaporator operating under 20 mm Hg vacuum and temperatures up to 120° C. The resulting reaction product was benzylated DETA, with viscosity, AHEW, theoretical amine value, and actual (measured) amine value properties, as shown in Table 1.

TABLE 1

Synthesis summary of benzylated polyalkylene polyamines

| Example # | 2 | 3 | 4 | 5 | 6 | 7 |
|---|---|---|---|---|---|---|
| Amine(s) used | DETA | DETA/TETA (70/30 wt) | TETA | EDA | N4 amine | N4/DETA/TETA (66/22/12 wt) |
| Degree of benzylation | 1.2:1 | 1.3:1 | 1.5:1 | 1.1:1 | 1.2:1 | 2.0:1 |
| Amine quantity (g) | 340.6 | 1904/816 | 292 | 180.3 | 325 | 267.3/89.1/49.5 |
| Benzaldehyde (g) | 420.2 | 3318 | 318 | 350.1 | 238 | 584.2 |
| Pd/C catalyst (g) | 5 | 41 | 5 | 2.7 | 5 | 6.5 |
| Viscosity at 25° C. (mPa · s) | 30 | 31 | 135 | 11 | 66 | 94 |
| AHEW | 52 | 56 | 62 | 60 | 61 | 86 |
| Theoretical amine value (mg KOH/g) | 797 | 794 | 799 | 667 | 781 | 664 |

TABLE 1-continued

Synthesis summary of benzylated polyalkylene polyamines

| Example # | 2 | 3 | 4 | 5 | 6 | 7 |
|---|---|---|---|---|---|---|
| Actual amine value (mg KOH/g) | 776 | 763 | 760 | 629 | 785 | 629 |

Example 3: Synthesis of Benzylated DETA/TETA (70 wt % of Diethylenetriamine and 30 wt % of Triethylenetetramine) at a Level of 1.3 Moles Benzaldehyde Per Mole of Amine (Average) (1.3:1 Molar Ratio)

Example 3 utilized the same process as described in Example 2, but with a mixture of 70/30 wt DETA and TETA as the polyalkylene component. The molar ratio of benzaldehyde to amine was 1.3:1. Table 1 lists the AHEW, viscosity and amine value properties of the benzylated DETA/TETA.

Example 4: Synthesis of Benzylated Triethylenetetramine (TETA) at 1.5:1 Molar Ratio Example 4 utilized the same process as described in Example 2, but with TETA as the polyalkylene component. The molar ratio of benzaldehyde to amine was 1.5:1. Table 1 lists the AHEW, viscosity and amine value properties of the benzylated TETA.

Example 5: Synthesis of Benzylated Ethylenediamine (EDA) at a 1.1:1 Molar Ratio Example 5 utilized the same process as described in Example 2, but with EDA as the polyalkylene component. The molar ratio of benzaldehyde to amine was 1.1:1. Table 1 lists the AHEW, viscosity and amine value properties of the benzylated EDA.

Example 6: Synthesis of Benzylated N4 at 1.2:1 Molar Ratio

Example 6 utilized the same process as described in Example 2, but with EDA as the polyalkylene component. The molar ratio of benzaldehyde to amine was 1.2:1. Table 1 lists the AHEW, viscosity and amine value properties of the benzylated N4.

Example 7: Synthesis of Benzylated N4 Amine/DETA/TETA at a Level of 2.0 Moles Benzaldehyde Per Mole of Amine (Average) (2.0:1 Molar Ratio)

Example 7 utilized the same process as described in Example 2, but with N4 amine (Example 1)/DETA/TETA at weight ratio of 66/22/12 as the polyalkylene polyamine compound. Table 1 lists the AHEW, viscosity and amine value properties of the benzylated N4 amine/DETA/TETA.

Example 8: Synthesis of Aminopropylated Benzyl Amine (Monobenzylated Propylene Diamine, or N-benzyl Propylenediamine)

Example 8 utilized the same process as described in Example 1, but with benzyl amine as the starting material to be cyanoethylated then hydrogenated. In the first step, benzyl amine (purchased from Aldrich Chemicals) 391 g was reacted with 203 g acrylonitrile in the presence of 12 g water to generated cyanoethylated benzyl amine. In the second step, cyanoethylated benzyl amine 437 g from first step in 316 g of isopropyl alcohol and 24 g water was hydrogenated in the presence of 8.8 g of Raney Co catalyst and 2.6 g of LiOH. The product was analyzed by GC-MS and NMR to contain 93% of desired product aminopropylated benzyl amine (monobenzylated propylene diamine). The product has a calculated HEW of 55, and theoretical amine value of 1026 mgKOH/g.

Example 9: Synthesis of Mannich Base of Cardanol with Dimethylamine

To a 1-liter glass reactor equipped with a nitrogen inlet, an overhead stirrer, a condenser, and an additional funnel, was charged cardanol (300 g, 1 mol, purchased from Palmer International), dimethyl amine (40% in water, 135.2 g, 1.2 mol, purchased from Aldrich), and isopropanol (315 g). To the reaction mixture was added formaldehyde (37% in water, 97.3 g, 1.2 mol, purchased from Aldrich) via the additional funnel. The reaction was exotherm, and was cooled with a water bath to maintain temperature below 60° C. After the formaldehyde addition, the reaction was heated at 60° C. for 2 additional hours. The reaction was then subjected to atmosphere distillation to remove isopropanol and water at 85° C. to 115° C., and then vacuum distillation at 115° C. to remove all water. $^{13}C$ NMR of the product in $CDCl_3$ indicated the product as of the dimethy aminomethyl substituted cardanol at the position ortho to the hydroxyl group and para to the C15 chain. No unreacted cardanol was detected.

Example 10: Synthesis of Mannich Base of p-Cresol with Dimethylamine

Example 10 utilized the same process as described in Example 9, but with p-cresol (250 g, 2.3 mol, purchased from Aldrich), dimethyl amine (40% in water, 625.4 g, 5.5 mol, purchased from Aldrich), methanol (250 g), and formaldehyde (37% in water, 450 g, 5.5 mol, purchased from Aldrich). $^{13}C$ NMR of the product in $CDCl_3$ indicated the product as of the di-substituted and mono-substituted dimethyl aminomethyl at the position ortho to the hydroxyl as 76/24 mol ratio. No unreacted cresol was detected.

Example 11: Transamination of Ancamine® K54 with Benzylated DETA/TETA of Example 3 at 1:3 Molar Ratio To a 3-liter glass reactor equipped with a nitrogen inlet, an overhead stirrer, and a moisture trap adapter (purchased from Ace Glass). The top of the moisture trap adapter was attached to a dry-ice cold trap, and the bottom of the adapter was connected to a round-bottom flask with 50% acetic acid solution. The round-bottom flask was cooled in an ice bath. To the reactor was added Ancamine® K54 (750 g, 2.83 mol)

and benzylated DETA/TETA of Example 3 (1894 g, 8.49 mol). The reaction was heated up slowly to 140° C., and the evolving dimethylamine (DMA) was condensed by the dry-ice trap and collected in cold acetic acid solution. The reaction was carried out for 4.5 hours, and a total of 295.9 g of DMA was collected. The product was a light amber liquid with a viscosity of 5052 centipoise at 25° C., an amine value of 685 mgKOH/g, and a calculated HEW of 92. $^{13}$C NMR of the product in CDCl$_3$ indicated that the product contained, on average, 75 mol % of methylene dimethylamine amine-exchanged (transaminated) with benzylated DETA/TETA, 19 mol % residual unreacted methylene diamethylamine, 5 mol % unsubstituted para sites to hydroxyl group, and 2 mol % of unsubstituted ortho sites to hydroxyl group. This gives an average of 2.25 substituents of methylene-benzylated DETA/TETA per molecule.

Example 12: Transamination of Ancamine® K54 with Benzylated DETA/TETA of Example 3 at 1:2 Molar Ratio Example 12 utilized the same process as described in Example 11. The product was a light amber liquid with a viscosity of 198,000 centipoise at 25° C., an amine value of 643 mgKOH/g, and a calculated HEW of 128. $^{13}$C NMR of the product in CDCl$_3$ indicated that the product contained, on average, 75 mol % of methylene dimethylamine amine-exchanged (transaminated) with benzylated DETA/TETA, 18 mol % residual unreacted methylene diamethylamine, 6 mol % unsubstituted para sites to hydroxyl group, and 1 mol % of unsubstituted ortho sites to hydroxyl group. This gives an average of 2.25 substituents of methylene-benzylated DETA/TETA per molecule.

Example 13: Transamination of Ancamine® K54 with Benzylated DETA/TETA of Example 3 at 1:4.5 Molar Ratio Example 13 utilized the same process as described in Example 11. The product was a light amber liquid with a viscosity of 135 centipoise at 25° C., an amine value of 660 mgKOH/g, and a calculated HEW of 77. $^{13}$C NMR of the product in CDCl$_3$ indicated that the product contained, on average, 86 mol % of methylene dimethylamine amine-exchanged (transaminated) with benzylated DETA/TETA, 4 mol % residual unreacted methylene diamethylamine, 5 mol % unsubstituted para sites to hydroxyl group, and 5 mol % of unsubstituted ortho sites to hydroxyl group. This gives an average of 2.58 substituents of methylene-benzylated DETA/TETA per molecule.

Example 14: Transamination of Ancamine® K54 with a Mixture of 60/40 Molar Ratio of Benzylated DETA/TETA of Example 3 and 3-(Diethylamino)Propylene Amine (DEAPA) at 1:3.0 Molar Ratio Example 14 utilized the same process as described in Example 11. The product was a light amber liquid with a viscosity of 1030 centipoise at 25° C., an amine value of 651 mgKOH/g, and a calculated HEW of 107. $^{13}$C NMR of the product in CDCl$_3$ indicated that the product contained on average 51 mol % of methylene dimethylamine amine-exchanged (transaminated) with benzylated DETA/TETA, 22 mol % of methylene dimethylamine amine-exchanged (transaminated) with DEAPA, 21 mol % residual unreacted methylene diamethylamine, 5 mol % unsubstituted para sites to hydroxyl group, and 1 mol % of unsubstituted ortho sites to hydroxyl group. This gives an average of 1.53 substituents of methylene-benzylated DETA/TETA per molecule, and 0.66 substituents of methylene-DEAPA per molecule.

Compared to Example 11, Example 14 clearly shows that under the same molar ratio of amine to Mannich base, and similar reaction conversion, co-exchange of benzylated DETA/TETA and DEAPA with Ancamine® K54 results in a product with much lower viscosity.

Example 15: Transamination of Ancamine® K54 with a Mixture of 60/40 Molar Ratio of Benzylated DETA/TETA of Example 3 and 3-(diethylamino)propylene Amine (DEAPA) at 1:2.0 Molar Ratio Example 15 utilized the same process as described in Example 11. The product was a light amber liquid with a viscosity of 6970 centipoise at 25° C., an amine value of 616 mgKOH/g, and a calculated HEW of 160. $^{13}$C NMR of the product in CDCl$_3$ indicated that the product contained on average 45 mol % of methylene dimethylamine amine-exchanged (transaminated) with benzylated DETA/TETA, 19 mol % of methylene dimethylamine amine-exchanged (transaminated) with DEAPA, 29 mol % residual unreacted methylene diamethylamine, 5 mol % unsubstituted para sites to hydroxyl group, and 1 mol % of unsubstituted ortho sites to hydroxyl group. This gives an average of 1.35 substituents of methylene-benzylated DETA/TETA per molecule, and 0.57 substituents of methylene-DEAPA per molecule.

Example 16: Transamination of Ancamine® K54 with a Mixture of 60/40 Molar Ratio of Benzylated DETA/TETA of Example 3 and 3-(diethylamino)propylene Amine (DEAPA) at 1:4.5 Molar Ratio Example 16 utilized the same process as described in Example 11. The product was a light amber liquid with a viscosity of 214 centipoise at 25° C., an amine value of 682 mgKOH/g, and a calculated HEW of 101. $^{13}$C NMR of the product in CDCl$_3$ indicated that the product contained on average 55 mol % of methylene dimethylamine amine-exchanged (transaminated) with benzylated DETA/TETA, 26 mol % of methylene dimethylamine amine-exchanged (transaminated) with DEAPA, 12 mol % residual unreacted methylene diamethylamine, 5 mol % unsubstituted para sites to hydroxyl group, and 1 mol % of unsubstituted ortho sites to hydroxyl group. This gives an average of 1.65 substituents of methylene-benzylated DETA/TETA per molecule, and 0.78 substituents of methylene-DEAPA per molecule.

Example 17: Transamination of Ancamine® K54 with Benzylated N4 Amine/DETA/TETA of Example 7 at 1:3 Molar Ratio Example 17 utilized the same process as described in Example 11. The product was a light amber liquid with a viscosity of 9010 centipoise at 25° C., an amine value of 546 mgKOH/g, and a calculated HEW of 137. $^{13}$C NMR of the product in CDCl$_3$ indicated that the product contained on average 78 mol % of methylene dimethylamine amine-exchanged (transaminated) with benzylated N4 amine/DETA/TETA, 17 mol % residual unreacted methylene diamethylamine, and 5 mol % unsubstituted para sites to hydroxyl group. This gives an average of 2.34 substituents of methylene-benzylated N4 amine/DETA/TETA per molecule, and 0.78 substituents of methylene-DEAPA per molecule.

Example 18: Transamination of Ancamine® K54 with Monobenzylated Ethylenediamine (N-benzyl Ethylenediamine) at 1:3 Molar Ratio Example 18 utilized the same process as described in Example 11. The product was a light amber liquid with a viscosity of 1793 centipoise at 25° C., and an amine value of 557 mgKOH/g, and a calculated HEW of 120. $^{13}$C NMR of the product in CDCl$_3$ indicated that the product contained on average 72 mol % of methylene dimethylamine amine-exchanged (transaminated) with benzylated ethylenediamine, 22 mol % residual unreacted methylene diamethylamine, 5 mol % unsubstituted para sites to hydroxyl group, and 1 mol % unsubstituted ortho sites to hydroxyl group. This gives an average of 2.16 substituents of methylene-monobenzylated ethylenediamine per molecule.

Example 19: Transamination of Ancamine® K54 with Monobenzylated Propylenediamine (N-benzyl Propylenediamine) at 1:3 Molar Ratio Example 19 utilized the same process as described in Example 11. The product was a light amber liquid with a viscosity of 6570 centipoise at 25° C., an amine value of 537 mgKOH/g, and a calculated HEW of 109. $^{13}$C NMR of the product in CDCl$_3$ indicated that the product contained on average 88 mol % of methylene dimethylamine amine-exchanged (transaminated) with benzylated ethylenediamine, 6 mol % residual unreacted methylene diamethylamine, and 6 mol % unsubstituted para sites to hydroxyl group. This gives an average of 2.64 substituents of methylene-monobenzylated propylenediamine per molecule.

Example 20: Transamination of Ancamine® K54 with a Mixture of 60/40 Molar Ratio of Benzylated DETA/TETA of Example 3 and 3-(dimethylamino)propylene Amine (DMAPA) at 1:3 Molar Ratio Example 20 utilized the same process as described in Example 11 but with vacuum distillation to remove unreacted DMAPA. The product was a light amber liquid with a viscosity of 14670 centipoise at 25° C., and an amine value of 619 mgKOH/g, and a calculated HEW of 104. $^{13}$C NMR of the product in CDCl$_3$ indicated that the product contained on average 59 mol % of methylene dimethylamine amine-exchanged (transaminated) with benzylated DETA/TETA, 22 mol % of methylene dimethylamine amine-exchanged (transaminated) with DMAPA, 11 mol % residual unreacted methylene diamethylamine, 6 mol % unsubstituted para sites to hydroxyl group, and 1 mol % of unsubstituted ortho sites to hydroxyl group. This gives an average of 1.77 substituents of methylene-benzylated DETA/TETA per molecule, and 0.66 substituents of methylene-DMAPA per molecule.

Example 21: Transamination of Ancamine® K54 with a Mixture of 50/50 Molar Ratio of Benzylated DETA/TETA of Example 3 and N,N-Dimethyldipropylenetriamine (DMAPAPA) at 1:3 Molar Ratio Example 21 utilized the same process as described in Example 11. The product was a light amber liquid with a viscosity of 851 centipoise at 25° C., and an amine value of 731 mgKOH/g, and a calculated HEW of 98. $^{13}$C NMR of the product in CDCl$_3$ indicated that the product contained on average 42 mol % of methylene dimethylamine amine-exchanged (transaminated) with benzylated DETA/TETA, 32 mol % of methylene dimethylamine amine-exchanged (transaminated) with DMAPAPA, 21 mol % residual unreacted methylene diamethylamine, and 5 mol % unsubstituted para sites to hydroxyl group. This gives an average of 1.26 substituents of methylene-benzylated DETA/TETA per molecule, and 0.96 substituents of methylene-DMAPAPA per molecule.

Example 22: Transamination of Ancamine® K54 with a Mixture of 70/30 Molar Ratio of Benzylated DETA/TETA of Example 3 and Bis(dimethylaminopropyl)amine (N,N,N',N'-Tetramethyldipropylenetriamine) at 1:3 Molar Ratio Example 22 utilized the same process as described in Example 11. Bis(dimethylaminopropyl)amine (or N,N,N',N'-Tetramethyldipropylenetriamine) was purchased from Aldrich. The final reaction product was a light amber liquid with a viscosity of 2123 centipoise at 25° C., amine value of 660 mgKOH/g, and a calculated HEW of 132. $^{13}$C NMR of the product in CDCl$_3$ indicated that the product contained on average 67 mol % of methylene dimethylamine amine-exchanged (transaminated) with benzylated DETA/TETA, 8 mol % of methylene dimethylamine amine-exchanged (transaminated) with Bis(dimethylaminopropyl)amine, 20 mol % residual unreacted methylene diamethylamine, and 6 mol % unsubstituted para sites to hydroxyl group. This gives an average of 2.01 substituents of methylene-benzylated DETA/TETA per molecule, and 0.18 substituents of methylene-bis(dimethylaminopropyl)amine per molecule.

Example 23: Transamination of Mannich Base of Example 9 with Benzylated DETA/TETA of Example 3 at 1:1 Molar Ratio Example 23 utilized the same process as described in Example 11. The final reaction product was an amber liquid with a viscosity of 257 centipoise at 25° C., an amine value of 330 mgKOH/g, and a calculated HEW of 182. $^{13}$C NMR of the product in CDCl$_3$ indicated that the product contained on average 66 mol % of methylene dimethylamine amine-exchanged (transaminated) with benzylated DETA/TETA, 30 mol % residual unreacted methylene diamethylamine, and 4 mol % of unsubstituted ortho sites to hydroxyl group. This gives an average of 0.66 substituents of methylene-benzylated DETA/TETA per molecule.

Example 24: Transamination of Mannich Base of Example 10 with a Mixture of 60/40 Molar Ratio of Benzylated DETA/TETA of Example 3 and 3-(diethylamino)propylene Amine (DEAPA) at 1:2 Molar Ratio Example 24 utilized the same process as described in Example 11. The final reaction product was a light amber liquid with a viscosity of 440 centipoise at 25° C., an amine value of 595 mgKOH/g, and a calculated HEW of 120. $^{13}$C NMR of the product in CDCl$_3$ indicated that the product contained on average 50 mol % of methylene dimethylamine amine-exchanged (transaminated) with benzylated DETA/TETA, 21 mol % of methylene dimethylamine amine-exchanged (transaminated) with DEAPA, 16 mol % residual unreacted methylene diamethylamine, and 12 mol % of unsubstituted ortho sites to hydroxyl group. This gives an average of 1.0 substituents of methylene-benzylated DETA/TETA per molecule, and 0.42 methylene-DEAPA per molecule.

Example 25: Transamination of Ancamine® K54 with a Mixture of 50/50 Molar Ratio of Benzylated DETA/TETA of Example 3 and N,N-bis(3-aminopropyl)methylamine (N-methyldipropylenetriamine, or methyliminobis(N-propylamine) at 1:3 Molar Ratio Example 25 utilized the same process as described in Example 11. N-bis(3-aminopropyl)methylamine (or N-methyldipropylenetriamine) was purchased from TCI America. The final reaction product was a light amber liquid with a viscosity of 2817 centipoise at 25° C., an amine value of 739 mgKOH/g, and a calculated HEW of 79. $^{13}$C NMR of the product in CDCl$_3$ indicated that the product contained on average 35 mol % of methylene dimethylamine amine-exchanged (transaminated) with benzylated DETA/TETA, 47 mol % of methylene dimethylamine amine-exchanged (transaminated) with N,N-bis(3-aminopropyl)methylamine, 11 mol % residual unreacted methylene diamethylamine, 5 mol % unsubstituted para sites to hydroxyl group, and 2 mol % unsubstituted ortho sites to hydroxyl group. This gives an average of 1.05 substituents of methylene-benzylated DETA/TETA per molecule, and 1.41 substituents of methylene-N,N-bis(3-aminopropyl)methylamine per molecule.

Example 26: Transamination of Ancamine® K54 with a Mixture of 50/50 Molar Ratio of Benzylated DETA/TETA of Example 3 and 3-aminopropylcyclohexylamine (APCHA, N-Cyclohexyl-1,3-propanediamine) at 1:3 Molar Ratio Example 26 utilized the same process as described in Example 11. APCHA was purchased from Aldrich. The final reaction product was a light amber liquid with a viscosity of 4405 centipoise at 25° C., an amine value of 611 mgKOH/g, and a calculated HEW of 120. $^{13}$C NMR of the product in CDCl$_3$ indicated that the product contained on average 46 mol % of methylene dimethylamine amine-exchanged (transaminated) with benzylated DETA/TETA, 32 mol % of methylene dimethylamine amine-exchanged (transaminated) with APCHA, 16 mol % residual unreacted methylene diamethylamine, 5 mol % unsubstituted para sites to hydroxyl group, and 1 mol % unsubstituted ortho sites to hydroxyl group. This gives an average of 1.38 substituents of methylene-benzylated DETA/TETA per molecule, and 0.96 substituents of methylene-APCHA per molecule.

Testing Examples

Curing agent mixtures were prepared by combining and mixing the components given in examples. They were then thoroughly mixed stoichiometrically and thoroughly (amine/epoxy ratio was 1:1) with the epoxy component of standard bisphenol-A based epoxy resin of Epon 828, EEW 190, unless specified otherwise. The curing agents were tested neat or in 40% benzyl alcohol as specified in examples. Comparative Example 1 (C1) is a commercially available fast Mannich base curing agent derived from MXDA and was used in 50% benzyl alcohol as recommended, with an HEW of 98. Benzylated DETA/TETA of Example 3 either neat or in 40% benzyl alcohol was used as Comparative Example 2 (C2), and benzylated N4 amine/DETA/TETA of Example 7 either neat or in 40% benzyl alcohol was used as Comparative Example 3 (C3). The term "ND" in tables stands for "not determined" because the coatings were too soft or too tacky to carry out measurements. Test methods are summarized in Table 2.

TABLE 2

| | Test Methods | |
|---|---|---|
| Property | Response | Test Method |
| Gel time | 150 gram sample | D2471 |
| Drying time: BK recorder | Thin film set times phases 2 & 3 (hour) | ASTM D5895 |
| Specular gloss | Gloss at 20° and 60° | ASTM D523 |
| Persoz pendulum hardness | Persoz hardness (s) | ASTM D4366 |
| Shore D hardness | Shore D | ASTM D2240 |
| Mechanical property | Tensile strength | D638 Type I |
| | Conical bending | ASTM D522 |
| | Cylindrical bending | ASTM D522 |

In test examples 1-4 the curing agent was prepared in 40% benzyl alcohol. In text example 5, curing agent was used neat without benzyl alcohol.

Test Example 1. Gel Time, Dry Time and Persoz Hardness of Clear Coatings

The gel time characterizes the time a composition transitions from a liquid to a gel. The gel time of the amine-epoxy compositions was measured with a TECHNE gelation timer model FGT 6 using ASTM D2471. The dry time or thin film set time (TFST) was determined using a Beck-Koller recorder, in accordance with ASTM D5895. The amine-epoxy coatings were prepared on standard glass panels at a wet film thickness of about 75 micron WFT (wet film thickness) using a Bird applicator resulting in dry film thicknesses from 60 to 70 microns. The coatings were cured at 23° C. and 5° C. and 50% relative humidity (RH). The data for curing agents with 40% benzyl alcohol are summarized in Table 3. The coatings containing the curing agent of the present invention had similar or shorter dry times, and similar or better Persoz hardness development than the comparative known fast Mannich base curing agent based on MXDA at both 23° C. and 5° C., and faster dry time than non-Mannich base benzylated polyalkylene polyamines, and all coatings showed high gloss value. Non-Mannich base benzylated polyalkylene polyamines in comparative examples C2 and C3 gave clear coating at 23° C. but cured slowly, and did not cure properly at 5° C. and produced tacky coatings, while known fast Mannich base curing agent based on MXDA comparative examples C1 gave fast dry time, however coating appearance at low temperature was poor, the coating showed low gloss value. The results clearly show that the coatings containing the curing agent of the present invention possess both fast cure and good coating appearance, indicative of good compatibility between curing agent and epoxy resin.

TABLE 3

Test summary of gel time, dry time, Persoz hardness and surface appearance properties of clear coatings

| Property | | | Ex 11 | Ex 12 | Ex 13 | Ex 14 | Ex 15 | Ex 16 |
|---|---|---|---|---|---|---|---|---|
| Gel time (min.) | | | 25 | 19 | 26 | 27 | 23 | 30 |
| TFST (h) (23° C.) | Ph 2 | | 1.8 | 1.2 | 3.2 | 1.7 | 1.2 | 2.5 |
| | Ph 3 | | 3.2 | 3.1 | 5.0 | 3.0 | 2.8 | 4.0 |
| TFST (h) (5° C.) | Ph 2 | | 8.0 | 4.5 | 14.5 | 7.5 | 5.0 | 10.5 |
| | Ph 3 | | 9.0 | 9.5 | 21 | 10 | 7 | 14.5 |
| Persoz (23° C.) | 24 h | | 227 | 249 | 135 | 210 | 65 | 229 |
| 6 mil WFT | 7 d | | 278 | 310 | 276 | 249 | 88 | 271 |
| Coating appearance (23° C.) | | | clear | clear | clear | clear | clear | clear |
| Persoz (5° C.) | 24 h | | 15 | 25 | 11 | 12 | 14 | 8 |
| 6 mil WFT | 2 d | | 45 | 55 | 15 | 58 | 32 | 23 |
| | 7 d | | 138 | 206 | 55 | 180 | 38 | 41 |
| Gloss (23° C.) (60°) | 7 d | | 100 | 100 | 100 | 100 | 100 | 100 |
| Gloss (5° C.) (60°) | 7 d | | 100 | 100 | 100 | 100 | 100 | 100 |
| Coating appearance (5° C.) | | | clear no blush | clear no blush | clear no blush | clear no blush | clear no blush | clear no blush |

| Property | | | C1 | C2 | C3 |
|---|---|---|---|---|---|
| Gel time (min.) | | | 21 | 33 | 45 |
| TFST (h) (23° C.) | Ph 2 | | 1.7 | 5.0 | 6.3 |
| | Ph 3 | | 3.0 | 6.8 | 7.1 |
| TFST (h) (5° C.) | Ph 2 | | 7 | 14.5 | >24 |
| | Ph 3 | | 10.5 | 17.5 | >24 |
| Persoz (23° C.) | 24 h | | 296 | 225 | 340 |
| 6 mil WFT | 7 d | | 294 | 310 | 350 |
| Coating appearance (23° C.) | | | slight haze | clear | clear |
| Persoz (5° C.) | 24 h | | 62 | tacky | tacky |
| 6 mil WFT | 7 d | | 175 | 130 | 186 |
| Specular Gloss (23° C.) (60°) | 7 d | | 100 | 100 | 103 |
| Specular Gloss (5° C.) (60°) | 7 d | | 84 | 68 | 90 |
| Coating appearance (5° C.) | | | haze slight blush | tacky slight blush | tacky slight blush |

Test Example 2. Carbamation Resistance Test

Clear coatings were applied to clean Lenata chart at a wet film thickness of about 75 micron WFT (wet film thickness) using a Bird applicator. Lenata chart was cleaned with ethanol before use. The coatings were cured at 23° C. and 5° C. and 50% relative humidity (RH) for 1 day, 2 days, and 7 days. A lint free cotton patch was placed on the test panel, ensuring that it is at least 12 mm from the edge of the panel. The cotton patch was dampened with 2-3 ml of de-mineralized water and covered with a suitable lid (e.g. watch glass). The panel was left undisturbed for the specified time (standard time is 24 h). After that time, the patch was removed and the coating was dried with a cloth or tissue. The panel was examined immediately for carbamation and rated according to numbers listed below. The data is summarized in Table 4. The data indicates that the coatings cured with the curing agents of the present invention have improved carbamation resistance especially at low temperature of 5° C. than those made from the known fast Mannich base curing agent.

TABLE 4

Summary of carbamation test

| Application Temperature | | Ex 11 | Ex 14 | Ex 15 | C1 | C2 | C3 |
|---|---|---|---|---|---|---|---|
| 23° C. | 24 hrs | 5 | 5 | 5 | 3 | 2 | 3 |
| | 7 d | 5 | 5 | 5 | 4 | 4 | 5 |
| 5° C. | 24 hrs | 3 | 5 | 4 | 2 | 1 | 2 |
| | 7 d | 5 | 5 | 5 | 3 | 3 | 4 |

1 - Very bad White surface
2 - Bad Slight whitening
3 - Moderate Hazy surface
4 - Good Visible contours
5 - Very good Glossy surface Test Example 3. Mechanical Property Test Tensile test was conducted according to ASTM D638 type I. Cylindrical mandrel bending and conical mandrel bending panels were prepared on cold rolled steel panels with dry film thickness of 75 microns and cured at 23° C. for 7 days before testing. Cylindrical mandrel bending was performed using Model 266 from Erichsen and conical mandrel was performed on Model 312 from Erichsen. The bend time was about 1-2 seconds to determine crack resistance. The data is summarized in Table 5. The results indicate that epoxy cured with the curing agents of the present invention have similar mechanical properties to those made from the known fast Mannich base curing agent.

TABLE 5

| Mechanical property test | | | | |
|---|---|---|---|---|
| Mechanical Property | | Ex 12 | Ex 13 | C1 |
| Tensile strength | MPa | 40 | 35 | 36 |
| Tensile Modulus | MPa | 2320 | 2020 | 2100 |

TABLE 5-continued

| Mechanical property test | | | | |
|---|---|---|---|---|
| Mechanical Property | | Ex 12 | Ex 13 | C1 |
| Cylindrical bending | mm cylinder | 32 | >32 | 32 |
| Conical bending | failure | Full length | Full length | Full length |

Test Example 4. Dry Time and Persoz Hardness of Clear Coatings Cured with Curing Agents without Benzyl Alcohol The test protocols are the same as in Test Example 1. The data is summarized in Table 6. The coatings containing the curing agent of the present invention had shorter dry times than the non-Mannich base benzylated polyalkylene polyamines in comparative examples C2 and C3 at both 23° C. and 5° C., especially at 5° C. The results clearly show that the coatings containing the curing agent of the present invention possess both fast cure and gave clear coatings with good coating appearance, indicative of good compatibility between curing agent and epoxy resin.

Test Example 5: Degree of Cure of Epoxy-Amine Compositions

Degree of cure and glass transition temperature Tg were determined by Differential Scanning calorimetry (DSC). About 5 grams of the amine-epoxy composition was mixed 3 cycles using FlackTeK DAC 250 SP SpeedMixer™ by Hauschild. Around 5-10 mg samples were placed in Tzero hermetic DSC pans and were sealed in air. The samples were analyzed using a TA Instruments Q2000 DSC calibrated in T4P mode at a heating rate of 10° C./minute with Indium. The samples were heated from −80° C. to 280° C. at 10° C./minute. The samples were then cooled back to −90° C. and the test was repeated. The degree of cure was determined by subtracting the residual heat of cure after 7 days from the initial total heat of cure, then divided by the initial total heat of cure. Table 7 lists the degree of cure and Tg of epoxy-amine compositions. Table 7 indicates that the curing agent of the present invention had high degree of cure both at 23° C. and 5° C., and Tg was similar to the known fast Mannich base curing agent.

TABLE 6

Dry time, Persoz hardness and surface appearance properties of clear coatings without benzyl alcohol

| Property | Ex 18 | Ex 20 | Ex 22 | Ex 24 | Ex 26 | C2 | C3 |
|---|---|---|---|---|---|---|---|
| TFST (h) (23° C.) | | | | | | | |
| phase 2 | 3.2 | 1.9 | 1.8 | 4.3 | 3.4 | 3.8 | 5.3 |
| phase 3 | 3.6 | 2.5 | 2.4 | 5.0 | 4.3 | 5.7 | 7.4 |
| TFST (h) (5° C.) | | | | | | | |
| phase 2 | 7.3 | 4.0 | 4.0 | 9.5 | 6.3 | 11.8 | 11.6 |
| phase 3 | 9.8 | 5.0 | 4.5 | 11.0 | 10.0 | 14.6 | 15.0 |
| Persoz 7 day @ 23° C. | 373 | 375 | 366 | 386 | 332 | soft | soft |
| Gloss (@ 23° C.) (20°/60°) | 171/156 | 178/160 | 159/154 | 145/148 | 119/150 | ND* | ND* |
| Coating Appearance @ 23° C. | clear | clear | clear | clear | clear | clear | clear |
| Persoz 7 day @5° C. | 338 | 362 | 314 | 342 | 225 | soft-tacky | soft-tacky |
| Gloss (5° C.) (20°/60°) | 182/161 | 154/148 | 106/118 | 145/146 | 116/125 | ND* | ND* |
| Coating Appearance @ 5° C. | clear | clear | clear | clear | clear | hazy | hazy |

ND: not determined because coatings were too soft or tacky

TABLE 7

Degree of cure and Tg of epoxy-amine compositions

| | | Ex 12 | Ex 13 | C1 |
|---|---|---|---|---|
| DSC Tg 7 day cure | 5° C. | 41 | 40 | 45 |
| | 23° C. | 53 | 50 | 47 |
| DSC Degree of Cure (%) | 5° C. | 89.2 | 99.9 | 90.7 |
| | 23° C. | 95.2 | 99.3 | 99.0 |

All above-mentioned references are hereby incorporated by reference herein.

While the invention has been described with reference to certain aspects or embodiments, it will be understood by those skilled in the art that various changes may be made and equivalents may be substituted for elements thereof without departing from the scope of the invention. In addition, many modifications may be made to adapt the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

The invention claimed is:

1. A benzylated Mannich base composition comprising at least one benzylated Mannich base compound, wherein the at least one benzylated Mannich base compound comprises a reaction product of (a) a substituted phenolic compound having a phenolic moiety and at least one substituent of formula (I):

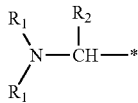

(I)

wherein $R_1$ is each independently a linear or branched alkyl group having 1 to 4 carbon atoms, and $R_2$ is hydrogen, methyl, ethyl or phenyl;

wherein the phenolic moiety is selected from the group consisting of phenols, ortho-, meta- and para-cresols, cardanol, the isomeric xylenols, para-tert-butylphenol, para-nonylphenol, 2,6-di-t-butylphenol, 2,4-di-t-butylphenol, 2-t-butylphenol, alpha-naphthol, beta-naphthol, diphenols or polyphenols, hydroquinone, 4,4'-dihydroxydiphenyl, 4,4'-dihydroxydiphenyl ether, 4,4'-dihydroxydiphenylsulfone, 4,4'-dihydroxydiphenylmethane, bisphenol A, the condensation products of phenol and formaldehyde, and combinations thereof, with (b) a benzylated polyalkylene polyamine having at least two nitrogen atoms, at least two active amine hydrogen atoms and at least one benzyl group of formula (II):

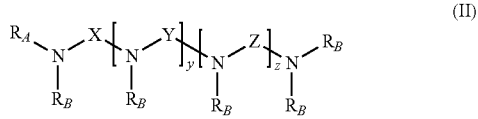

(II)

wherein $R_A$ is substituted or unsubstituted benzyl; $R_B$ is each independently $R_A$, or a hydrogen atom, or a group selected from $C_1$-$C16$ linear, cyclic, and branched alkyl, alkenyl, and alkaryl groups; X, Y, and Z are independently selected from $C_2$-$C_{10}$ alkylene, and cycloalkylene groups; y is an integer from 0 to 7, and z is an integer from 0 to 4; and, optionally, (c) at least one multifunctional amine having at least two nitrogen atoms and at least two active amine hydrogen atoms per molecule; and wherein the at least one benzylated Mannich base compound has at least two nitrogen atoms, at least two active amine hydrogen atoms and at least one benzyl group per compound.

2. The composition of claim 1, wherein the substituted phenolic compound includes compounds according to formulas selected from the group consisting of:

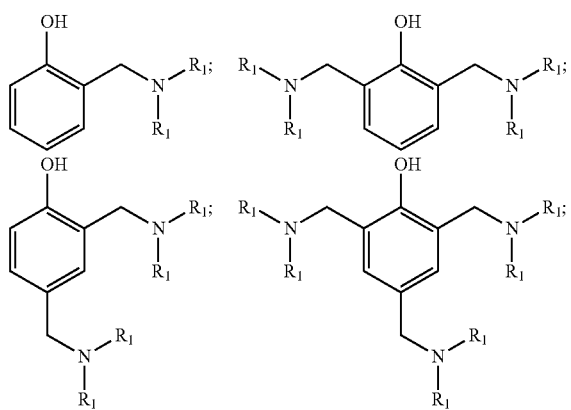

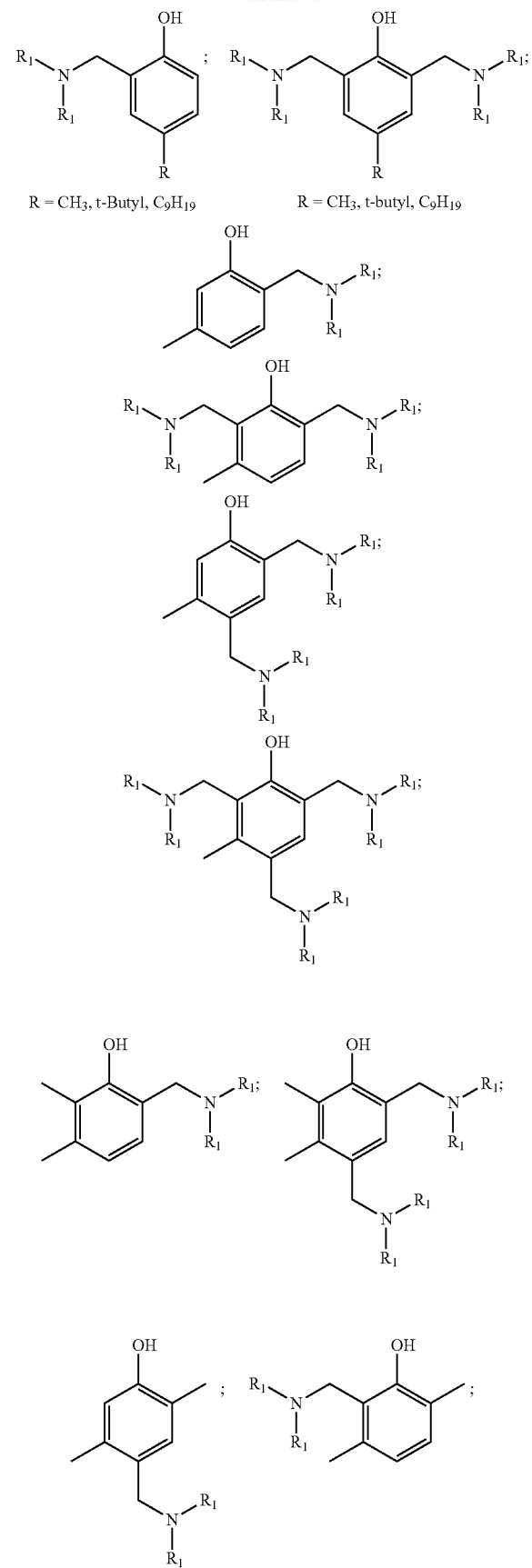

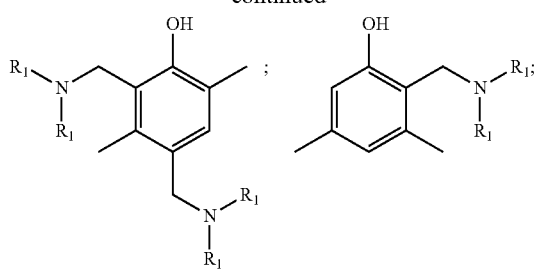

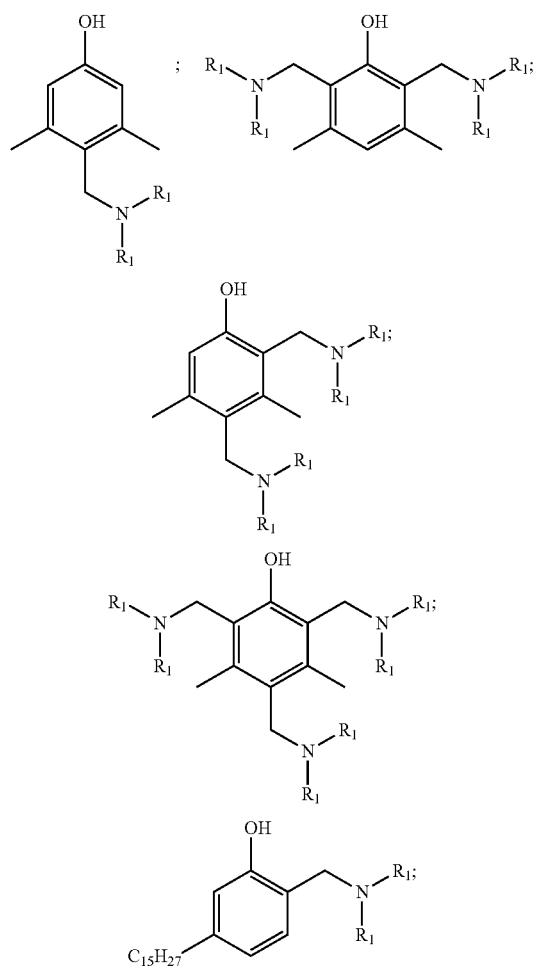

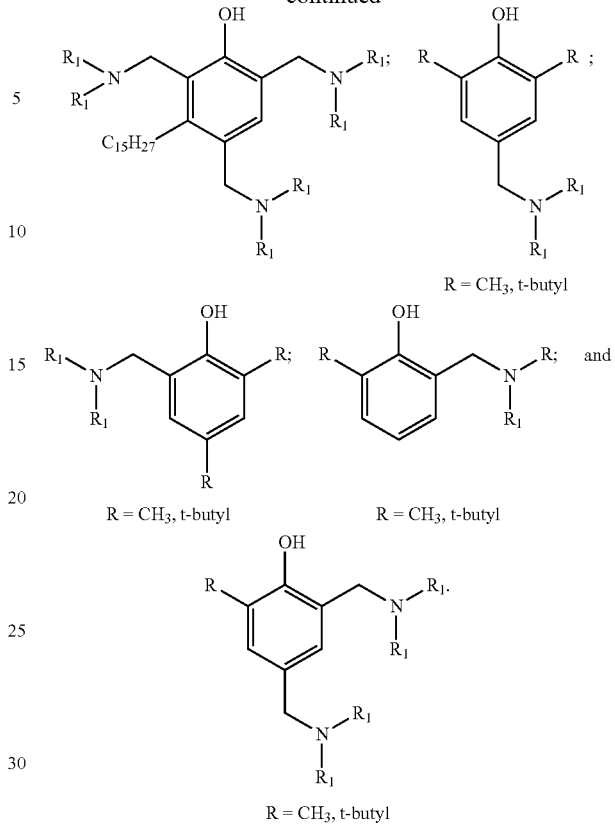

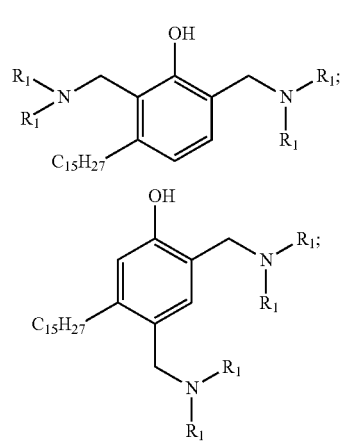

3. The composition of claim 1, wherein the benzylated polyalkylene polyamine is selected from the group consisting of benzylated polyethylene polyamine, benzylated polypropylene polyamine, benzylated polyethylene-polypropylene polyamines, and combinations thereof.

4. The composition of claim 1, wherein the benzylated polyalkylene polyamine is selected from the group consisting of benzylated ethylene diamine, benzylated diethylenetriamine, and benzylated triethylenetetramine, benzylated tetraethylenepentamine, benzylated propylene diamine, benzylated dipropylenetriamine, benzylated tripropylenetetramine, benzylated N3, benzylated N4, benzylated N5, and combinations thereof.

5. The composition of claim 1, wherein the benzylated polyalkylene polyamine is polyethylene polyamine represented by formula (II), wherein X, Y, and Z are ethylene, y and z are integers of 0 to 4, $R_A$ is benzyl or vanillyl, and $R_B$ is hydrogen or benzyl.

6. The composition of claim 1, wherein the benzylated polyalkylene polyamine is a polyethylene-polypropylene polyamine represented by formula (II), wherein X, and Z are propylene, and Y is ethylene, y is 1 or 2, and z is 1, 2, 3 or 4, $R_A$ is benzyl or vanillyl, and $R_B$ is hydrogen or benzyl.

7. The composition of claim 1, wherein the benzylated polyalkylene polyamine is a polypropylene polyamine represented by formula (II), wherein X, Y and Z are propylene, y is 0, 1 or 2, and z is 1, 2, or 3, $R_A$ is benzyl or vanillyl, and $R_B$ is hydrogen or benzyl.

8. The composition of claim 1, wherein the at least one multifunctional amine is an aliphatic polyamine according to one or more of formulae (III), (IV), and (V):

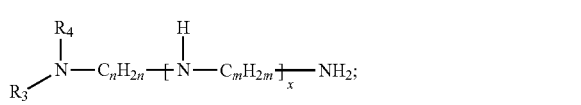 (III)

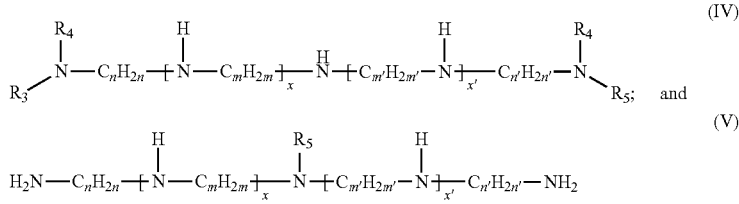 (IV) and

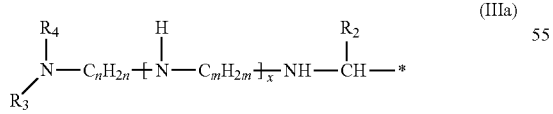 (V)

wherein $R_4$ and $R_3$ are each independently hydrogen atoms, linear or branched alkyl group having 1 to 8 carbon atoms, cycloalkyl group having 4 to 10 carbon atoms, or together form a radical of formula —$(CH_2)_5$—, or —$(CH_2CH_2)$—O—$(CH_2CH_2)$—, and $R_4$ and $R_3$ cannot both be hydrogen atoms; $R_5$ is a linear or branched alkyl group having 1 to 8 carbon atoms, or cycloalkyl group having 4 to 10 carbon atoms; m, m', n and n' are integers from 2 to 5, and x and x' are integers from 0 to 3.

9. The composition of claim 8, wherein $R_4$ and $R_3$ are methyl, ethyl, or propyl; $R_5$ is an alkyl group having 1 to 4 carbon atoms, or cycloalkyl group having 6 to 8 carbon atoms; m, m', n, and n' are 2, 3 or 4; and x and x' are 0 or 1.

10. The composition of claim 8, wherein $R_4$ is hydrogen; $R_3$ is a cyclohexyl; and $R_5$ is an alkyl group having 1 to 4 carbon atoms, or cycloalkyl group having 6 to 8 carbon atoms; m, m', n, and n' are 2, 3 or 4; and x and x' are 0 or 1.

11. The composition of claim 8, wherein $R_4$ and $R_3$ are both methyl or ethyl; $R_5$ is methyl, ethyl, or cyclohexyl; m, m', n, and n' are 2, 3 or 4; and x and x' are 0 or 1.

12. The composition of claim 1, wherein the at least one multifunctional amine is selected from the group consisting of an aliphatic polyamine, a cycloaliphatic polyamine, an arylaliphatic polyamine, an aromatic polyamine, a polyether amine, a Mannich base derivative of an aliphatic amine, a cycloaliphatic amine, an aromatic amine, polyamide or amidoamine derivative of an aliphatic amine, a cycloaliphatic amine, or an aromatic amine, amine adduct derivatives of an aliphatic amine, a cycloaliphatic amine, or an aromatic amine, and combinations thereof.

13. The composition of claim 1, wherein the reaction product includes less than one substituent of formula (IIIa):

 (IIIa)

wherein $R_4$ and $R_3$ are each independently linear or branched alkyl group having 1 to 8 carbon atoms, cycloalkyl group having 4 to 10 carbon atoms, or together form a radical of formula —$(CH_2)_5$—, or —$(CH_2CH_2)$—O—$(CH_2CH_2)$—, $R_2$ is hydrogen, methyl, ethyl or phenyl, m, and n are integers from 2 to 5, and x is an integer from 0 to 3.

14. The composition of claim 1, wherein the reaction product includes at least one substituent of formula (IIa):

$$\text{Formula (II)} - \underset{\underset{R_2}{|}}{C}H - * \quad \text{(IIa)}$$

wherein Formula (II) is attached to the carbon atom via any nitrogen atom of the Formula (II).

15. A curing agent composition comprising the contact product of:
(a) the benzylated Mannich base composition of claim 1, and
(b) at least one multifunctional amine having two or more active amine hydrogens per molecule.

16. The curing agent composition of claim 15, wherein the composition includes an amine hydrogen equivalent weight (AHEW) based on 100% solids from about 30 to about 500.

17. An epoxy system comprising the reaction product of:
(a) a curing agent composition comprising the benzylated Mannich base composition of claim 1, and
(b) an epoxy composition comprising at least one multifunctional epoxy resin.

18. An article of manufacture comprising the system of claim 17.

19. A process for the preparation of benzylated Mannich base compositions, the process comprising reacting:
a substituted phenolic compound having at least one substituent of formula (I):

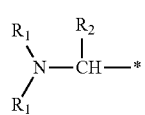 (I)

wherein $R_1$ is each independently a linear or branched alkyl group having 1 to 4 carbon atoms, and $R_2$ is hydrogen, methyl, ethyl or phenyl; with
(b) a benzylated polyethylene polyamine; and
(c) optionally a multifunctional amine having at least two nitrogen atoms and at least two active amine hydrogen atoms per molecule.

* * * * *